(12) United States Patent
Tucker et al.

(10) Patent No.: US 7,731,969 B1
(45) Date of Patent: Jun. 8, 2010

(54) METHODS FOR DEVELOPING AND PRODUCING ANTIGEN-SPECIFIC ANTIBODY-PRODUCING CELLS

(75) Inventors: Ward C. Tucker, Madison, WI (US); Mark W. Jackson, Oregon, WI (US); Rachel H. Kravitz, Madison, WI (US)

(73) Assignee: NeoClone Biotechnology International, LLC, Madison, WI (US)

( * ) Notice: Subject to any disclaimer, the term of this patent is extended or adjusted under 35 U.S.C. 154(b) by 83 days.

(21) Appl. No.: 11/951,387

(22) Filed: Dec. 6, 2007

Related U.S. Application Data

(60) Provisional application No. 60/873,154, filed on Dec. 6, 2006.

(51) Int. Cl.
*A61K 39/00* (2006.01)
*A61K 35/28* (2006.01)
*C12N 5/06* (2006.01)
*C12N 5/00* (2006.01)

(52) U.S. Cl. .................. 424/184.1; 424/577; 435/326; 435/346; 435/372

(58) Field of Classification Search .................. None
See application file for complete search history.

(56) References Cited

U.S. PATENT DOCUMENTS

| 5,244,656 | A | 9/1993 | Risser et al. |
|---|---|---|---|
| 5,705,150 | A | 1/1998 | Risser et al. |

OTHER PUBLICATIONS

Arce, Sergio et al; CD38 low IgG-secreting cells are precursors of various CD38 high-expressing plasma cell populations; Journal of Leukocyte Biology; vol. 75, Jun. 2004; pp. 1022-1028.
Bovia, Fabrice et al, Efficient transduction of primary human B lymphocytes and nondividing myeloma B cells with HIV-1-derived lentiviral vectors; Blood, Mar. 1, 2003; vol. 101, No. 5, pp. 1727-1733.
Driver, David J. et al; Development and Maintenance of a B220-Memory B Cell Compartment; The Journal of Immunology, 2001; vol. 167; pp. 1393-1405.
Ettinger, Rachel et al; IL-21 Induces Differentiation of Human Naive and Memory B Cells into Antibody-Secreting Plasma Cells; The Journal of Immunology, 2005; vol. 176; pp. 7867-7879.
Hasbold, Jhagvaral et al; Evidence from the generation of immunoglobulin G-secreting cells that stochastic mechanisms regulat lymphocyte differentiation; Nature Immunology, Jan. 2004; vol. 5, No. 1: pp. 55-63.
Hathcock, Karen S. et al; Expression of Different CD45 Isoforms by Subpopulations of Activated B Cells; The Journal of Immunology; Oct. 1, 1992; vol. 149, No. 7, pp. 2286-2294.
Hausl, Christina et al; Long-term Persistence of Anti-factor VIII Antibody-secreting Cells in Hemophilic Mice after Treatment with Human Factor VIII; Thromb Haemost, 2002; vol. 87; pp. 840-845.
Hausl, Christina et al; Preventing restimulation of memory B cells in hemophilia A; a potential new strategy for the treatment of antibody-dependent immune disorders; Blood; Jul. 1, 2004; vol. 104, No. 1, pp. 115-122.
Hausl, Christina et al; High-dose factor VIII inhibits factor VIII-specific memory B cells in hemophilia A with factor VIII inhibitors; Blood; Nov. 15, 2005; vol. 106, No. 10, pp. 3415-3422.
Kodituwakku, Aruna P. et al; Isolation of antigen-specific B cells; Immunology and Cell Biology; 2003, vol. 81;pp. 163-170.
Kwekkeboom, J. et al; CD40 plays an essential role in the activation of human B cells by murine EL4B5 cells; Immunology; 1993; vol. 79, pp. 439-444.
Largaespada, David A. et al; The ABL-MYC retrovirus generates antigen-specific plasmacytomas by in vitro infection of activated B lymphocytes from spleen and other murine lymphoid organs; Journal of Immunological Methods; vol. 197; 1996, pp. 85-95.
McHeyzer-Williams, Louise J. et al; Antigen-specific B Cell Memory: Expression and Replenishment of a Novel B220- Memory B Cell Compartment; J. Exp. Med., Apr. 3, 2000; vol. 191, No. 7, pp. 1149-1165.
Ohno, Shinsuke et al; Chromosomal Translocations Activating myc Sequences and Tranduction of v-abl Are Critical Events in the Rapid Induction of Plasmacytomas by Pristane and Abelson Virus; Journal of Experimental Medicine; Jun. 1984; vol. 159; pp. 1762-1777.
Ozaki, Katsutoshi et al; Regulation of B Cell Differentiation and Plasma Cell Generation by IL-21, a Novel Inducer of Blimp-1 and Bcl-6; The Journal of Immunology; 2004; vol. 173, pp. 5361-5371.
Potter, Michael; Neoplastic developent in plasma cells; Immunological Reviews, 2003, vol. 194, pp. 177-195.

(Continued)

*Primary Examiner*—Michail A Belyavskyi
(74) *Attorney, Agent, or Firm*—Andrus, Sceales, Starke & Sawall, LLP

(57) ABSTRACT

Disclosed are methods for producing immortalized antigen-specific plasma cells and antibodies which include depleting an immunized cell population of CD138-positive cells and activating the depleted cells. The methods may be used to improve the efficiency of obtaining immortalized antigen-specific plasma cells.

24 Claims, 11 Drawing Sheets

OTHER PUBLICATIONS

Ridderstad, Anna et al; The xid Mutation Diminishes Memory B Cell Generation but Does Not Affect Somatic Hypermutation and Selection; The Journal of Immunology, 1996; vol. 157, pp. 3357-3365.

Sanderson, Ralph D. et al; B lumphocytes express and lose syndecan at specific stages of differentiation; Cell Regulation, Nov. 1989; vol. 1, pp. 27-35.

Shapiro-Shelef, Miriam et al; Blimp-1 Is Required for the Formation of Immunoglobulin Secreting Plasma Cells and Pre-Plasma Memory B Cells; Immunity, Oct. 2003; vol. 19, pp. 607-620.

Shapiro-Shelef, Miriam et al; Blimp-1 is required for maintenance of long-lived plasma cells in the bone marrow; The Journal of Experimental Medicine; Dec. 5, 2005; vol. 202, No. 11, pp. 1471-1476.

Smith, Kenneth G.C. et al; The extent of affinity maturation differs between the memory and antibody-forming cell compartments in the primary immune response; The EMBO Journal, 1997; vol. 16, No. 11, pp. 2996-3006.

Snapper, Clifford M. et al; Interferon-# and B Cell Stimulatory Factor-1 Reciprocally Regulate Ig Isotype Production; Science, May 22, 1987; vol. 236, No. 4804, pp. 944-947.

Sze, Daniel M.-Y. et al; Intrinsic Constraint on Plasmablast Growth and Extrinsic Limits of Plasma Cell Survival; J. Exp. Med., Sep. 18, 2000; vol. 192, No. 6, pp. 813-821.

Tonkonogy, Susan L. et al; Effects of Lymphokines on Ig Production Depend on the State of Activation of the Responding B Cells; The Journal of Immunology; Jun. 15, 1989; vol. 142, No. 12, pp. 4351-4360.

Tucci, Alessandra et al; Effects of Eleven Cytokines and of IL-1 and Tumor Necrosis Factor Inhibitors in a Human B Cell Assay; The Journal of Immunology; May 1, 1992; vol. 148, No. 9, pp. 2778-2784.

Weissinger, Eva M. et al; Induction of plasmacytomas secreting antigen-specific monocloncal antibodies with a retrovirus expressing v-abl and c-myc; Proc. Natl. Acad. Immunology, Oct. 1991, vol. 88, pp. 8735-8739.

Werner-Favre, Christiane et al; IgG subclass switch capacity is low in switched and in IgM-only, but high in IgD +IgM+, post-germinal center (CD27*) human Be cells; Eur. J. Immunology; 2001, vol. 31, pp. 243-249.

Whitehead, Ian et al; Expression Cloning of Oncogenes by Retroviral Transfer of cDNA Libraries; Molecular and Cellular Biology; Feb. 1995; vol. 15, No. 2, pp. 704-710.

Wiener, Francis et al; Nonrandom Chromsomal Change (Trisomy 11) in Murine Plasmacytomas Induced by an ABL-MYC Retrovirus; Cancer Research, Mar. 1, 1995; vol. 55, pp. 1181-1188.

Zhang, Xiaohong et al; IL-4-Dependent IgE Switch in Membrane IgA-Positive Human B Cells; The Journal of Immunology; Nov. 1, 1991; vol. 147, No. 9, pp. 3001-3004.

Zubler, Rudolf H. et al; Mutant EL-4 Thymoma Cells Polycloncally Activate Murine and Human B Cells Via Direct Cell Interaction; The Journal of Immunology; Jun. 1985; vol. 134, No. 6, pp. 3662-3668.

Lalor, Paul A. et al; Functional and molecular characterization of single, (4-hydroxy-3-nitrophenyl)acetyl (NP)- specific, IgG1+ B cells from antibody-secreting and memory B cell pathways in the C57BL/6 immune response to NP*; Eur. J. Immunol. 1992, vol. 22, pp. 3001-3011.

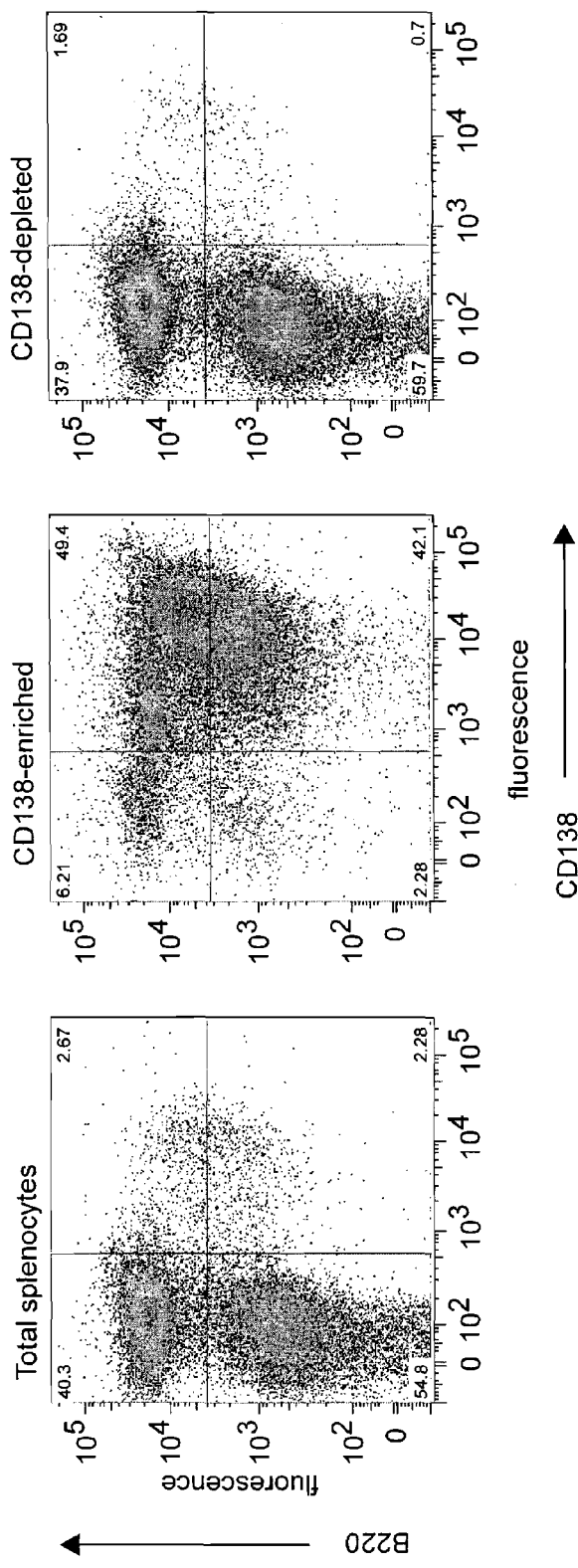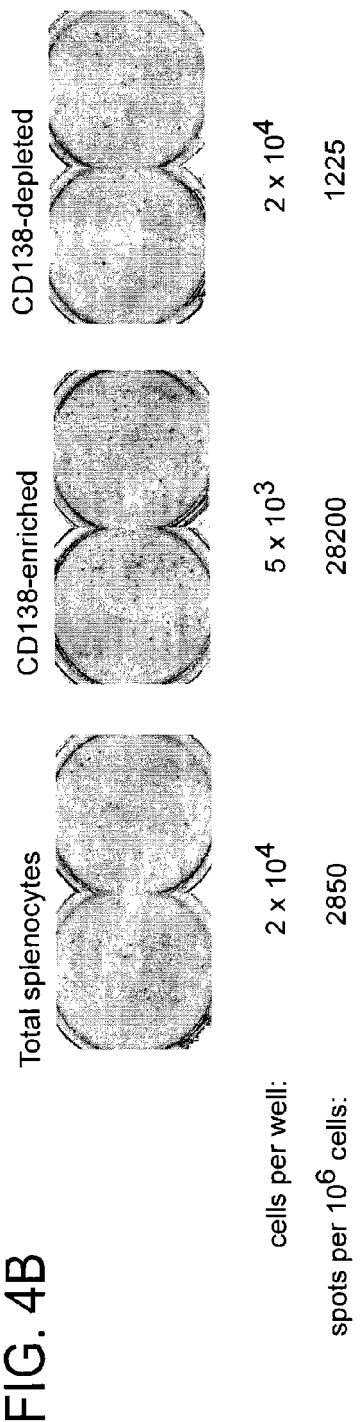
FIG. 4A
FIG. 4B

FIG. 6A
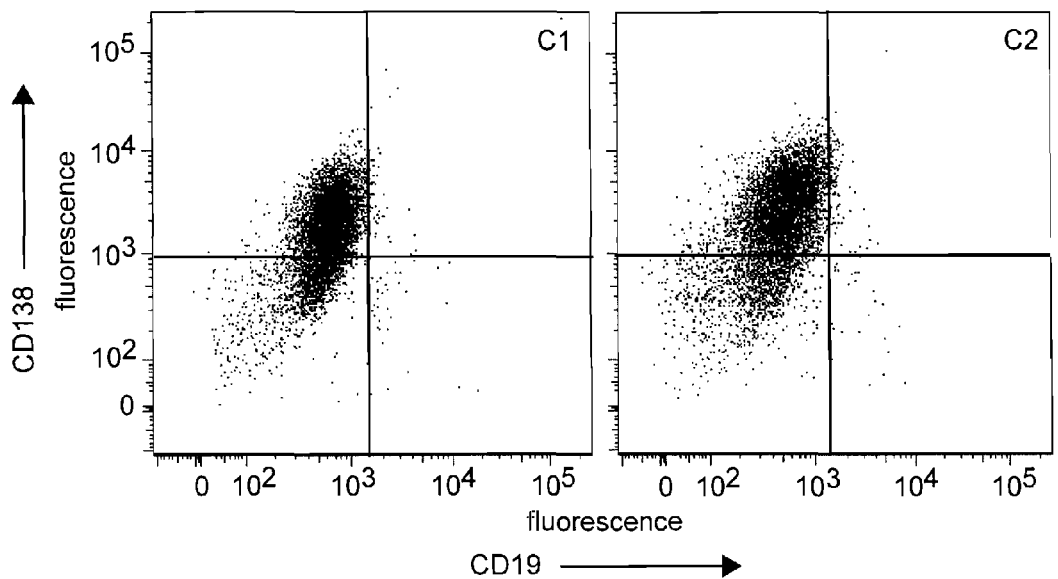
FIG. 6B
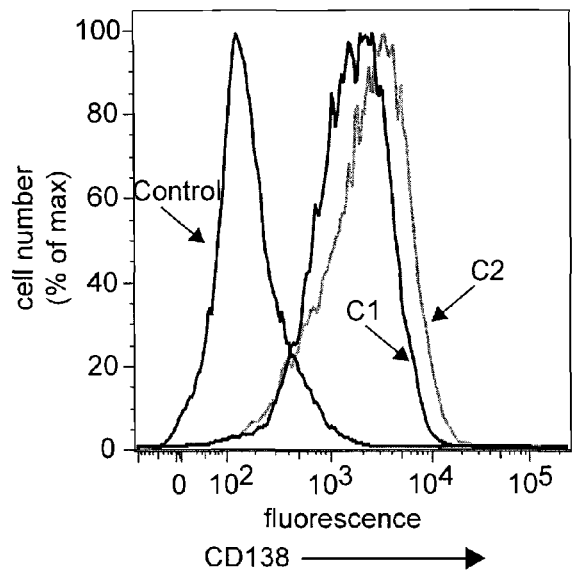
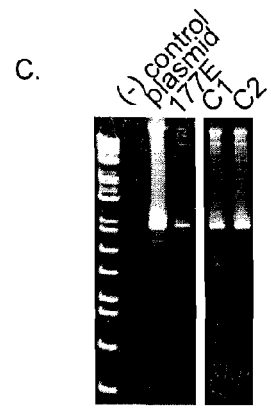
C.
D.
| cell line | total IgG (mg/mL) |
|---|---|
| C1 | 44.1 |
| C2 | 68.2 |
| 177E | 40.3 |

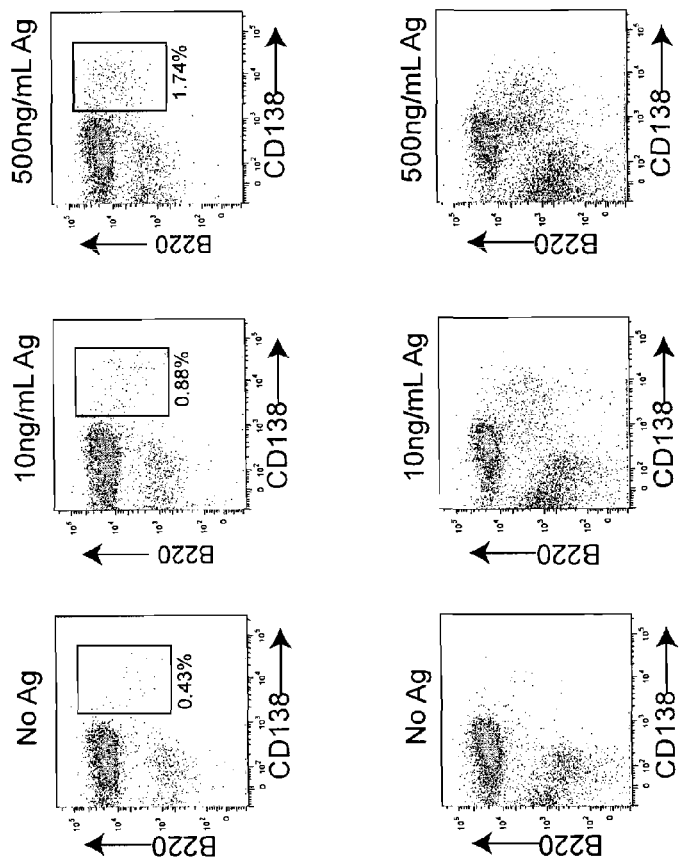
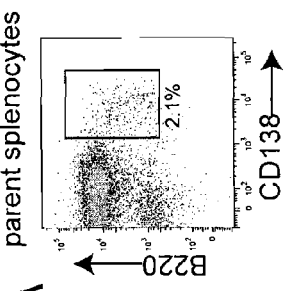
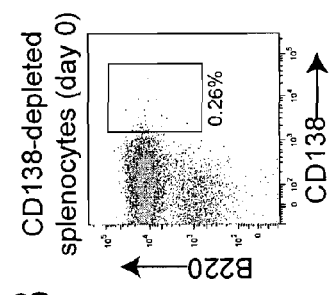

METHODS FOR DEVELOPING AND PRODUCING ANTIGEN-SPECIFIC ANTIBODY-PRODUCING CELLS

CROSS-REFERENCE TO RELATED APPLICATIONS

The present application claims the benefit under 35 U.S.C. §119(e) to U.S. provisional application No. 60/873,154, filed on Dec. 6, 2006, the content of which is incorporated herein by reference in its entirety.

BACKGROUND

The presently disclosed methods relate generally to the field of antibody development or production. In particular, the methods relate to the field of in vitro monoclonal antibody production.

Monoclonal antibodies (mAbs) are highly specific affinity reagents used for detecting and treating diseases. For example, mAbs may be used in localizing biomarkers in tissue, purifying biomarkers from complex substances, and measuring markers leading to diagnosis of diseases cancer in clinical samples (e.g., cancer). The need for mAbs as affinity reagents is continually growing with the advent of multi-analyte detection platforms such as protein microarrays. The advancement of these platforms has yielded the potential for fast, high-throughput analysis of complex samples for small molecules and proteins of interest. The next few years will likely see rapid advancement in the use of these platforms for cancer biomarker discovery and the early-stage diagnosis of different cancers.

Despite the advancement of multi-analyte platforms, the overall performance and usefulness of these approaches depends on the quality of the mAbs used to capture and detect molecules of interest on the microarray surface. Successful development of a microarray requires the screening of many mAbs for affinity, specificity, cross-reactivity, and platform compatibility. For a given target, dozens of mAbs may need to be screened, and thus the techniques used to generate the mAbs must be able to generate a panel of highly diverse antigen-specific (Ag-specific) mAbs. Currently, the means to develop mAbs are limited to a few different strategies, each with limited abilities to generate clonally diverse panels of Ag-specific mAbs.

The standard method for creating monoclonal antibodies to an antigen involves the creation of a fused cell called a "hybridoma." A hybridoma is produced by fusing together an established tumor cell line, such as a myeloma cell line, and an antibody-producing cell (e.g., a B-lymphocyte) from an animal that has previously been immunized with the antigen. Antibody-producing cells typically are obtained from the animal's spleen, lymph nodes, or lymph tissue (e.g., splenocytes or lymphocytes). These fused cells or "hybrid cells" then are selected and screened to obtain a hybridoma that produces the desired antibody (i.e., a "hybridoma").

Hybridoma technology has significant disadvantages. Typically, one hybridoma clone may be generated per $10^5$-$10^6$ splenocytes fused, thus most of the Ag-specific cells contained within the splenocyte population may be lost. In addition, many of the clones generated may not produce mAbs that recognize the antigen of interest. Furthermore, hybridoma cell lines of interest must be separated through screening and subcloning. The frequency of successful, Ag-specific B cell hybridomas may be on the order of one per $10^6$-$10^8$ starting cells. Finally, hybridomas are polyploid and chromosomally unstable. As a result, months of in vitro culture may be required to stabilize each clone and ensure strong mAb production.

An alternative to traditional hybridoma technology is phage display. Phages are viruses that infect bacteria such as *E. coli*. The phage genome is replicated within the bacteria, translocated to the cytoplasm and packaged into rod-shaped particles, which are then released into the media upon bacterial lysis. The particle coats can be engineered to "display" ligands such as antibodies. Thus large phage libraries containing billions of different antibody genes can be generated, with each phage containing a single antibody gene. These libraries can be screened for binding against any antigen of interest and the desired clone selected. A major advantage of phage display is that it does not require animal immunization. This also may be a primary drawback, because antibodies developed using naïve antibody phage libraries may have affinities that are generally two to three orders of magnitude lower than those of antibodies produced using traditional fusion technology. Increasing the probability of obtaining high-affinity antibodies with phage display requires additional mutagenesis upon clone selection, greatly increasing the naïve library size, or generating libraries from immunized animals. Each option requires extensive development time and expense.

Plasmacytoma technology may be used as an alternative to hybridoma technology and phage display technology. Plasmacytomas are immortalized, antibody producing cells. Plasmacytomas have been obtained by infecting B cells with an immortalizing retrovirus. For example, the ABL-MYC retrovirus has been used to produce plasmacytomas. ABL-MYC is a replication-defective retrovirus, which contains v-abl from the Abelson Murine Leukemia virus (Ab-MuLV) and murine c-myc. ABL-MYC infection stably transforms Ag-specific B cells into plasmacytomas that produce an antibody to a specified target antigen. Antigen-specific plasmacytomas may be obtained by infecting splenocytes from immunized mice with ABL-MYC and then subsequently injecting the infected splenocytes into recipient mice for plasmacytoma and ascites development. This process may provide antibodies against a wide range of antigens. However, clonal diversity may be limited by in vivo clonal selection, plasmacytoma development, and plasmacytoma propagation. For example, one disadvantage of plasmacytoma technology is that clonal diversity may be limited by in vivo ascites development. During plasmacytoma development, many Ag-specific clones may be lost to other clones with more aggressive growth characteristics. In addition, successful Ag-specific plasmacytoma development may depend on strong immune responses from the immunized mice upon antigen challenge. Antigens that elicit weak to moderate immune responses may be unlikely to develop Ag-specific plasmacytomas.

Thus, new methods for obtaining antigen-specific B-lymphocytes are desirable. In particular, new methods for selection and clonal expansion of antigen-specific B-cell populations to produce stable hybridomas and plasmacytomas are desirable.

SUMMARY

Disclosed are methods for producing immortalized antigen-specific plasma cells (i.e., plasmacytomas) and antibodies. The disclosed methods have been observed to produce an increased total number of immortalized plasma cells and a higher frequency of antigen-specific, immortalized plasma cells as compared to methods utilized in the prior art.

The methods typically may include the following steps: a) contacting lymphocytes and an antigen to obtain immunized cells (e.g., immunized B-lymphocytes); b) selecting the immunized cells based on expression of one or more cell surface markers or lack thereof (e.g., by depleting the immunized cells of CD138-positive cells); c) contacting the depleted population of immunized cells with an activating agent (e.g., the antigen, a cytokine, and/or immune cells); and d) immortalizing the activated cells, thereby producing the immortalized antigen-specific plasma cells. In some embodiments, the selected, activated immunized cells may be immortalized by fusing the selected, activated immunized cells and myeloma cells to obtain hybridoma cells. In other embodiments, the selected, activated immunized cells may be immortalized by transfecting the selected immunized cells with a viral vector that transforms the transfected cells to obtain plasmacytoma cells. The methods further may include culturing the immortalized antigen-specific plasma cells to obtain antibodies that bind specifically to the antigen (e.g., monoclonal antibodies).

The steps of the disclosed methods may be performed in vivo or ex vivo, either entirely or in part. In some embodiments, growing may include culturing the cells in vitro or transferring the cells into a host animal for growth and/or selection in vivo. In further embodiments, one or more steps of the methods may be performed in a host animal such as a mouse (e.g., a Balb/c mouse). The host animal may be immunodeficient, such as a mouse that has a severe combined immunodeficiency mutation (i.e., a SCID mouse).

In some embodiments, the methods for producing an immortalized antigen-specific plasma cell may include growing the selected immunized cells in the presence of an activating agent. Suitable activating agents may include cytokines as disclosed herein (e.g., IL-4) and antigens (e.g., the antigen utilized for immunizing the immunized cells as disclosed herein). In further embodiments, the selected immunized cells may be grown in the presence of the activating agent for at least 1 day (e.g., about 1-4 days or about 2-4 days).

The cells used in the methods may be obtained from any suitable source. In some embodiments, the lymphocytes may be obtained from one or more of spleen cells (e.g., splenocytes), peripheral blood leukocytes, bone marrow cells, and cord blood cells. Lymphocytes may include B-lineage lymphocytes (or "B cells"). The lymphocytes may be contacted with antigen to obtain immunized cells (e.g., immunized B lymphocytes), which subsequently are selected (e.g., by depleting the cells of CD138-positive cells); activated (e.g., by contacting the depleted cell with an activating agent); and immortalized (e.g., by fusion with a myeloma or by transfection with a transforming viral vector).

Typically, the immunized cells are selected prior to immortalization, which may include depleting the immunized cells of a sub-population of cells that express a cell surface marker. For example, the immunized cells may be selected using fluorescence-activated cell sorting ("FACS"). In some embodiments, the immunized cells may be selected based on expression or lack thereof of one or more cell surface markers (e.g., CD138, CD40, CD45, CD3e, CD11b, CD19, F4/80, CD79, and B220) to obtain one or more selected populations of immunized cells prior to immortalization. For example, the cells may be selected to obtain a CD138-enriched or a CD138-depleted population. In some embodiments, the immunized cells may be selected and separated into populations that exhibit relatively low CD138 expression and relatively high B220 expression (i.e., CD138$^{low}$/B220$^{high}$); populations that exhibit relatively high CD138 expression and intermediate B220 expression (i.e., CD138$^{high}$/B220$^{intermediate}$); or populations that exhibit relatively high CD138 expression and relatively low B220 expression (CD138$^{high}$/B220$^{low}$). In some embodiments, the immunized cells also may be selected to obtain a population of cells that is capable of being transformed at a relatively high efficiency (e.g., at least about 10%, 20%, 30%, 40%, 50%, 60%, 70%, 80%, or 90%). The immunized cells further may be selected and separated into populations based on relative expression of an antibody isotype (e.g., IgD). For example, selected populations may include B cells characterized as "naïve cells" (e.g., CD138$^{low}$/B220$^{high}$/IgD$^{high}$); "memory cells" (e.g., CD138$^{low}$/B220$^{high}$/IgD$^{low}$); "plasmablasts" (e.g., CD138$^{high}$/B220$^{intermediate}$/IgD$^{low}$) and "plasma cells" (e.g., CD138$^{high}$/B220$^{low}$/IgD$^{low}$).

In some embodiments, the immunized cells further may be grown in vitro prior to immortalization. For example, the immunized cells may be grown in vitro prior to immortalized to select a population of cells that is capable of being immortalized at a relatively high efficiency (e.g., at least about 10%, 20%, 30%, 40%, 50%, 60%, 70%, 80%, or 90%). In some embodiments, the immunized cells may be grown in vitro in the presence of one or more factors that may include cytokines (e.g., interleukins (such as IL-1, IL-2, IL-4, IL-5, IL-6, IL-10, and IL-21), interferons, growth factors, tumor necrosis factor (TNF)), cell surface ligands (e.g., CD40 ligand), antibodies (e.g., monoclonal antibodies against cell surface markers such as CD40 or IgM), and mitogens (e.g., pokeweed mitogen). The factor (e.g., a cytokine) may be recombinant, purified native, or unpurified native obtained from conditioned media (e.g., an unpurified cytokine from activated T cell/macrophage cultures). In further embodiments, the immunized cells may be activated with antigen in vitro prior to immortalization.

The immunized cells further may be grown in vitro in the presence of cells other than the immunized cells. For example, the immunized cells may be grown in the presence of antigen-specific T cells, dendritic cells, or macrophages. In some embodiments, the immunized cells may be grown on feeder layer cells (e.g., gamma-irradiated cells such as OP-9). The immunized cells may be grown with cells that are capable of activating the immunized cells to proliferate, differentiate, and/or secrete antibody. In some embodiments, the immunized cells are grown with a thymoma cell line such as the murine EL4 thymoma cell line, which optionally, may have been mutagenized. For example, the thymoma cell line may have been mutagenized to obtain bromo-deoxyuridine-resistant mutants (e.g., EL4-B5 cells). In some embodiments, the immunized cells are grown with macrophages (e.g., PD3188 cells or P388D1 cells) and/or T-cells. Optionally, the thymoma cells, macrophages, and/or T-cells may be stimulated or activated, for example with ultraviolet irradiation, phorbol 12-myristate 13-acetate (PMA), and/or phytohemagglutinin (PHA). Optionally, the thymoma cells, macrophages, and/or T-cells may be treated with gamma irradiation (e.g., to prevent proliferation).

In further embodiments, the immunized cells may be selected to obtain an antigen (Ag)-specific population (i.e., a population that secretes antibodies that specifically bind to the immunizing antigen). For example, the immunized cells may be selected by contacting the cells with the antigen to select an Ag-specific population. In some embodiments, the antigen is immobilized and the immunized cells are contacted with the immobilized antigen to select an Ag-specific population. In other embodiments, an Ag-specific population is selected by removing from the immunized cells those cells that are not Ag-specific, such as non-B cells and non-Ag-specific cells. For example, non-B cells and non-Ag-specific cells may be removed by contacting non-B cells and non-Ag-specific cells with labeled antibodies that bind specifically to a cell surface marker that characterizes the non-B cells or the non-Ag-specific cells.

In some embodiments, the immunized cells may be selected and activated to obtain a population of cells that subsequently is immortalized, where a significantly increased percentage of the immortalized cells are observed to produce antigen-specific antibodies as compared to methods utilized in the prior art. For example, the immunized cells may be selected or depleted based on the expression of a cell surface marker or the lack thereof (e.g., CD138) to obtain selected immunized cells which subsequently are immortalized. The immunized cells also may be grown in vitro in the presence of activating agents (e.g., cytokines such as IL-4 or Ag) prior to being immortalized. A relatively high percentage of the immortalized cells thus obtained may produce antigen-specific antibodies as compared to methods utilized in the prior art (e.g., up to a 10-fold increase in antigen-specific plasmacytomas may be obtained by the disclosed methods as compared to methods of the prior art that do not include selection and activation as disclosed herein).

In some embodiments, the methods include a) contacting B-lymphocytes with antigen to obtain immunized cells; b) optionally selecting the immunized cells based on expression of a cell surface marker or lack thereof; c) further contacting the immunized cells with antigen to obtain activated B-lymphocytes; d) transfecting the activated B-lymphocytes with a vector which transforms the transfected cells; and e) growing the transfected cells to obtain antibodies that specifically bind to the antigen. The methods typically result in the production of antigen-specific plasmacytomas. In some embodiments, transfecting the activated B-lymphocytes comprises transducing or infecting the activated B-lymphocytes with a virus vector. The activated B-lymphocytes may be transfected and subsequently grown to obtain antibodies that specifically bind to the antigen. Preferably, the activated B-lymphocytes are transfected by infecting the activated B-lymphocytes with a viral vector. Suitable virus vectors may include vectors derived from retroviruses (e.g., lentiviruses), herpes viruses (e.g., Epstein Barr virus and herpes simplex virus type 1), adenoviruses, and adeno-associated viruses. In other embodiments, the activated B-lymphocytes may be fused with a transformed cell (e.g., a myeloma cell) to obtain a hybridoma. The transfected cells or hybridomas may be grown in an in vivo system (e.g., in an animal host) or entirely in vitro under conditions described herein for growing and/or selecting antibody-producing cells.

Suitable virus vectors for use in the methods disclosed herein typically are capable of binding and infecting an activated lymphocyte. For example, the virus vector may include a retrovirus vector that comprises an envelope protein or glycoprotein for binding to a receptor present on B-lineage lymphocytes (e.g., mouse or human B lineage lymphocytes). The virus vector may be obtained by transfecting a suitable packaging cell line with a provirus (e.g., a provirus that expresses one or more oncogenes or protooncogenes). The virus vector may be a pseudotyped virus vector. Suitable packaging cell lines may include the murine psi-2 packaging cell line.

In some embodiments, the vector expresses one or more oncogenes or proto-oncogenes. Suitable oncogenes and proto-oncogenes may encode a polypeptide having c-myc activity, a polypeptide having v-abl activity, or both. In preferred embodiments, the vector expresses both a polypeptide having c-myc activity and a polypeptide having v-abl activity. In some embodiments, the vector may express the c-myc polypeptide and the mouse c-myc polypeptide, the v-abl polypeptide, variants of the c-myc polypeptide, or variants of the v-abl polypeptide. Variants of the c-myc polypeptide may include polypeptides having at least about 85% sequence or preferably at least about 95% sequence identity to the human or mouse c-myc polypeptide, where the variant has c-myc polypeptide activity. Variants of the v-abl polypeptide may include polypeptides having at least about 85% sequence identity or preferably at least about 95% sequence identity to the v-abl polypeptide, where the variant has v-abl polypeptide activity.

The methods typically include contacting lymphocytes with an antigen to obtain immunized cells and may include contacting immunized cells with antigen to obtain activated cells. The lymphocytes (or immunized cells) may be contacted directly with antigen or indirectly with antigen via antigen-presenting cells. For example, lymphocytes (or immunized cells) may be contacted with antigen by i) contacting antigen-presenting cells with the antigen; and ii) contacting the antigen-presenting cells with the lymphocytes (or immunized cells). Antigen-presenting cells may include dendritic cells, macrophage cells, B cells, or a mixture thereof. Preferably, the antigen-presenting cells comprise dendritic cells. Antigen-presenting cells may be obtained from any suitable source. In some embodiments, antigen-presenting cells are obtained from one or more of spleen cells (e.g., splenocytes), peripheral blood leukocytes, bone marrow cells, and cord blood cells. Preferably, the antibody-presenting cells are obtained from peripheral blood leukocytes.

The methods for producing antibodies may include selecting a clonal population of transformed, activated lymphocytes in vivo or ex vivo. For example, a clonal population may be selected by growing the cells and selecting those cells that produce an antibody that binds to the antigen specifically. In some embodiments, a clonal population may be selected by transferring and growing the transformed lymphocytes in a host animal (e.g., a SCID mouse). In another example, a clonal population may be selected by culturing the cells in vitro using conditions described herein for growing and/or selecting antibody-producing cells. In some embodiments, the clonal population may be further grown after selection, either in vivo or ex vivo, to obtain antibodies that specifically bind to the antigen.

The methods for producing antibodies may be used to obtain antibodies having a preferred affinity for the antigen. For example, the methods may be used to produce antibodies that specifically bind to the antigen with an affinity ($K_D$) of at least about $10^6$ $M^{-1}$, preferably at least about $10^8$ $M^{-1}$, and more preferably at least about $10^{10}$ $M^{-1}$.

The cells used in the methods disclosed herein may be human or non-human animal cells (e.g., mouse, rat, or rabbit cells). For example, B-lymphocytes, antigen presenting cells, immunized cells, infected cells, and other cells such as thymoma cells, macrophages, T cells, and stromal cells, may be human or non-human animal cells (e.g., mouse, rat, and rabbit cells).

Also disclosed are antibodies produced by the aforementioned methods. The antibodies may include monoclonal antibodies that specifically bind to a selected antigen. The antibodies may be formulated as a pharmaceutical composition for treating or diagnosing a disease or condition associated with the antigen. In some embodiments, the antibodies are conjugated to a therapeutic or diagnostic agent. The antibodies disclosed herein may be human antibodies or non-human antibodies (e.g., mouse, rat, and rabbit antibodies).

BRIEF DESCRIPTION OF THE DRAWINGS

FIG. 4 demonstrates enrichment of CD138$^{high}$ cells from murine splenocytes. Splenocytes isolated from RNA polymerase α-subunit immunized mice were subjected to magnetic enrichment using rat anti-mouse CD138 conjugated to phycoerythrin (PE; BD Biosciences) and EasySep PE Selection Kit (StemCell Technologies) according to the manufacturer's directions. A. Flow cytometry analysis of fraction splenocytes. Total splenocytes, CD138-enriched cells, and CD138-depleted cells ($10^6$ cells per sample) were stained using fluorophore-conjugated antibodies against CD138 and B220. B. CD138-enriched cells secrete Ag-specific Ig. ELISPOT assays were performed on serial dilutions of the indicated cells. The number of antigen-specific Ig specific cells per $10^6$ total cells is indicated below each well.

FIG. 6 demonstrates ABL-MYC transformation of activated B-lymphocytes in vitro. Splenocytes were treated with anti-CD40 and interleukins 4, 5 and 6 as described in FIG. 5 before injection with ABL-MYC. Infected cells were plated on OP-9 feeder cells in the presence of 10 ng/ml 11-6. After 21 (C1) and 45 (C2) days, two cell lines were isolated. Cells shown were gated for single cells. No CD3- or F4/80 CD11b-positive cells were observed. A. Histogram of CD expression for the samples shown in A. Control indicates non-stained C2 cells. C. Cell lines C1 and C2 contain integrated ALB-MYC. Genomic DNA was prepared from cell extracts and subjected to PCR analysis for ABL-MYC integration. A plasma containing ABL-MYC and plasmacytoma line 177E are shown as positive controls. The negative (−) control contained no DNA in the reaction tube. B. Cell lines C1 and C2 secrete IgG. Supernatants from 4- to 7-day cultures were analyzed for total IgG using Pierce's Easy-Titer IgG kit.

FIG. 7 indicates that CD138-depleted splenocytes can be activated in vitro to produce activated B-lymphocytes in response to antigen. Splenocytes isolated from mice immunized with the α-subunit of *E. coli* RNA polymerase (Ag) were magnetically depleted of CD138-positive cells using an anti-CD138 antibody conjugated to PE and StemCell Technologies EasySep PE-selection kit. Depleted cells ($5\times10^6$ cells/mL) were activated for 2 (day 2) or 4 (day 4) days in the presence of 20 ng/mL interleukin 4 along with 0, 10 or 500 ng/mL Ag. A. B220 and CD138 expression profile for parental splenocytes before magnetic depletion. Cells were stained with fluorophore-conjugated antibodies against the cell-determinant surface antigens CD45 (lymphocytes), B220 (B cells), CD138 (plasmablasts), CD11b (monocytes/macrophages) and CD3e (T cells) before analysis on a Beckman LSRII benchtop cytometer. Results for CD45-negative, CD3e-positive and CD11b-positive cells are not shown. CD138-positive cells (activated B-lymphocytes, including plasmablasts) are bracketed and the percentage of CD138-positive cells (as a function of the entire cell population) is indicated. B. B220 and CD138 expression profiles of CD138-depleted cells and in vitro activated cells. The percentage of CD138-positive cells was not analyzed for the day 4 cultures.

DETAILED DESCRIPTION

Figure 1:
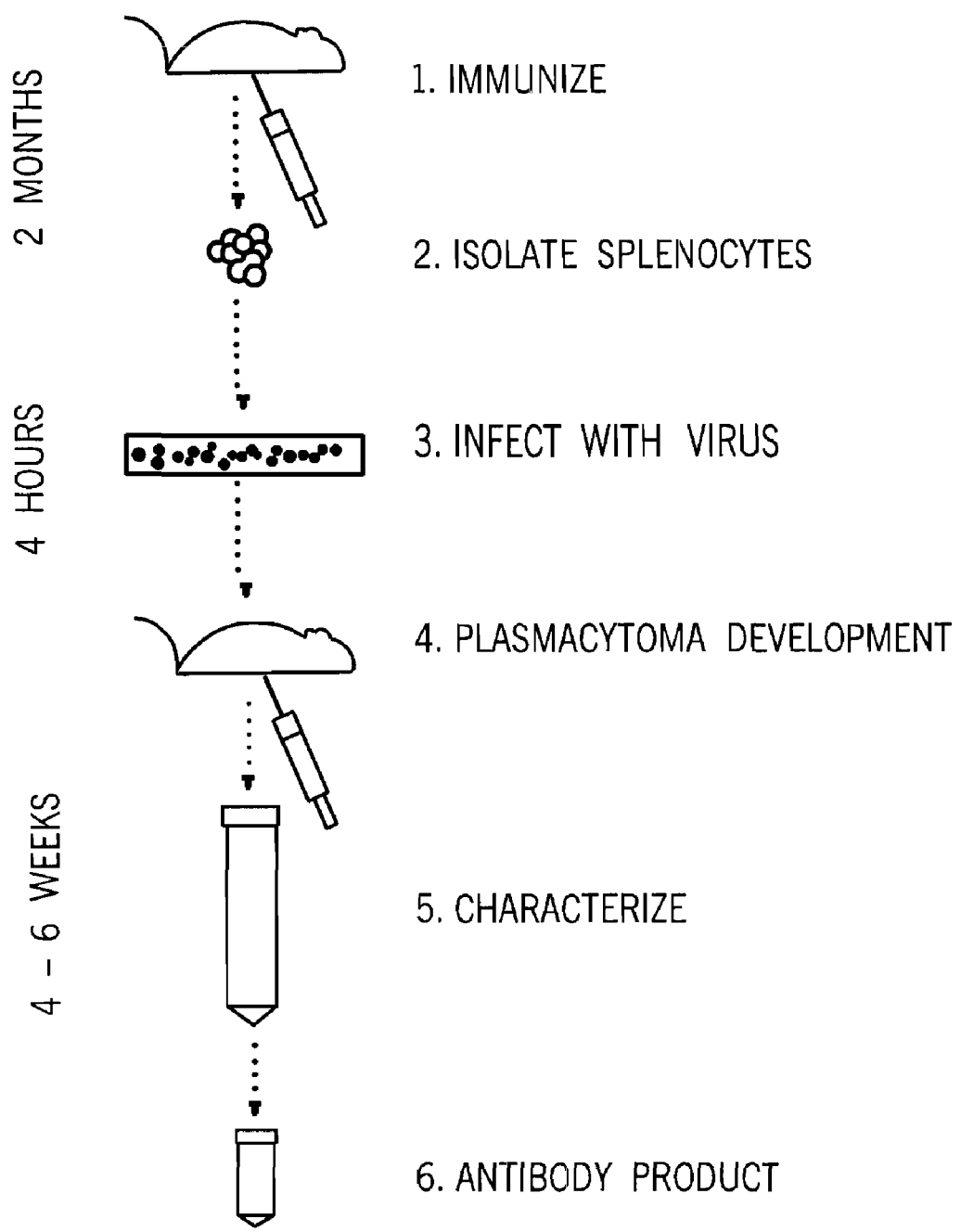
FIG. 1 is an exemplary method for producing monoclonal antibodies that includes in vivo plasmacytoma development.

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a" or "an" can mean one or more, depending upon the context in which it is used.

As used herein, "about", "substantially", and "approximately" will be understood by persons of ordinary skill in the art and will vary to some extent on the context in which they are used. If there are uses of the term which are not clear to persons of ordinary skill in the art given the context in which it is used, "about," "substantially," and "approximately" will mean plus or minus 10% of the particular term.

As used herein, "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The term "antibody" includes whole antibodies and any antigen binding fragment (i.e., "antigen-binding portion") or single chain thereof. An antibody may include a human or non-human antibody.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "monoclonal antibody" refers to antibodies displaying a single binding specificity which have variable and constant regions derived from germline immunoglobulin sequences.

The terms "antibody-producing cell" and "plasma cell" may be used interchangeably herein and refer to a type of white blood cell of the B-cell lineage that produces and secretes antibodies. As used herein "antibody-producing cell" and "plasma cell" may include immortalized antibody-producing cells and immortalized plasma cells. An antibody-producing cell or a plasma cell may be "antigen-specific" whereby the cell produces antibodies that bind specifically to a given antigen.

As used herein, "lymphocytes" are defined as cells involved in vertebrate immunity. These cells include the B lymphocytes (B cells), T lymphocytes (T cells), dendritic cells, and natural killer cells. Lymphocytes include immune cells isolated from blood, spleen, and lymph nodes. B-lymphocytes are immunoglobulin-expressing lymphocytes. These cells include, but are not limited to naïve B cells, memory B cells, plasmablasts, and plasma cells. The B-lymphocytes may actively secrete immunoglobulin or display the immunoglobulin on their cell surface. B-lymphocytes can express immunoglobulin M (IgM), immunoglobulin G (IgG), immunoglobulin A (IgA), immunoglobulin E (IgE), and immunoglobulin D (IgD). Activated, antigen-specific B-lymphocytes are said to express immunoglobulin with a high affinity for antigen. Activated lymphocytes are defined as lymphocytes which are actively undergoing cell division and expansion. Activated lymphocytes recognize antigen, present antigen, or express immunoglobulin against antigen in response to activating agents. Activating agents include, but are not limited to, antigen, cytokines, immunoglobulin, and/or other cells (e.g., lymphocytes).

As used herein, "specific binding" refers to antibody binding to a predetermined antigen. Typically, the antibody binds with an affinity corresponding to a $K_D$ of about $1 \times 10^{-6}$ M or less, and binds to the predetermined antigen with an affinity corresponding to a $K_D$ that is at least two orders of magnitude lower than its affinity for binding to a non-specific antigen (e.g., BSA, casein) other than the predetermined antigen or a closely-related antigen. The term "$K_D$" (M), as used herein, is intended to refer to the dissociation equilibrium constant of a particular antibody-antigen interaction.

The "percent identity" between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using mathematical algorithms.

As used herein, "transfecting" means introducing nucleic acid into a cell. "Transfecting" may include "infecting" and "transducing."

As used herein, "immortalization" means conversion of a normal cell into a cancerous cell. Immortalization may be performed by fusing a normal cell to a cancerous cell to obtain an immortalized hybrid cell or hybridoma. Immortalization also may be performed by "transformation", which means genetic alteration of a normal cell to a cancerous cell resulting from the introduction, uptake and expression of foreign genetic material. Immortalization may be performed by infecting a normal cell with a transforming viral vector to obtain a plasmacytoma.

As used herein, "ABL-MYC virus" refers to a replication defective retrovirus which contains v-abl form the Abelson Murine Leukemia virus (Ab-MuLV) and murine c-myc. (See U.S. Pat. Nos. 5,244,656 and 5,705,150, which are incorporated by reference herein in their entireties.) As used herein, "c-myc activity" and "v-abl activity" may include transforming activity.

Lymphocytes and Antigen-Presenting Cells

Lymphocytes (e.g., B-lymphocytes) and antigen-presenting cells may be obtained from any suitable source including non-human animals or human animals. For example, lymphocytes and antigen-presenting cell may be present within spleen cells (e.g., splenocytes), blood peripheral leukocytes, cord blood cells, and bone marrow cells. Lymphocytes may include B-lineage lymphocytes and T-lymphocytes. Antigen-presenting cells typically include dendritic cells, macrophage cells, and B-lineage lymphocytes.

In some examples, lymphocytes may be obtained from transgenic animals. For example, a lymphocyte may include a B cell obtained from a transgenic or transchromosomal non-human animal, e.g., a transgenic mouse, having a genome comprising a human heavy chain transgene and a light chain transgene.

Lymphocytes and antigen-presenting cells may be selected using fluorescence-activated cell sorting (FACS) based on selected cell markers. For example, a cell population may be enriched in or depleted of a subpopulation that includes a selected marker for example, CD138, CD40, CD45, CD3 (e.g., CD3e), CD11 (e.g., CD11b or CD11c), CD19, F4/80, CD79, B220, CD14, and CD86.

Virus Vectors

The term "vector," as used herein, is intended to refer to a nucleic acid molecule capable of transporting another nucleic acid to which it has been linked, i.e., a "transgene." One type of vector is a "viral vector," wherein additional nucleic acid segments or transgenes may be ligated into the viral genome or a portion of the viral genome and packaged into a virus or a replication defective virus. Viral vectors may include replication defective retroviruses, adenoviruses, adeno-associated viruses, and herpesviruses. A viral vector typically is capable of binding and entering a host cell and thereafter expressing a transgene. As such, the genome of a viral vector typically includes the minimum cis-elements for packaging the genome and expressing any transgene present therein. A viral vector may be prepared by transfecting a packaging cell line with a plasmid that includes the minimum cis-elements for packaging the genome and expressing any transgene present therein. The packaging cell line typically produces all of the proteins necessary for producing the virus vector (i.e., the trans-factors). The virus vector produced by a packaging cell line may include a homologous envelope glycoprotein or a heterologous envelope glycoprotein (i.e., the virus vector may be "pseudotyped"), which may alter the host cell range for the viral vector relative to the virus from which the virus vector is derived.

Retrovirus vectors are derived from retroviruses. The retrovirus genome and the associated proviral DNA minimally have three genes: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR typically contains all other cis-acting sequences necessary for viral replication. Some retroviruses, such as lentiviruses, have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

A packaging cell may be prepared by transfecting a suitable host cell with a first vector encoding a viral gag and a viral pol and another vector encoding a viral env. A packaging cell line may be prepared by transfecting a vector containing viral gag, pol, and env on a single vector. Suitable packaging cells include murine psi-2 cells. The viral env may be homologous or heterologous. Introducing a nucleic acid that includes the cis-elements and optionally a transgene, herein referred to as a "transfer vector," into the packaging cell yields a producer cell which releases infectious virus vector particles carrying the foreign gene of interest. The transfer vector may be transiently transfected or stably transfected into the packaging cell line.

Virus vectors are known in the art, see, e.g., Weissinger, et al., PNAS (1991), 88:8735-8739; Naldini et al., Sci. (1996) 272:263 267; and Zufferey et al., Nat. Biotech. (1997) 15:871 875. Generally the vectors are plasmid-based or virus-based, and are configured to carry the essential sequences for incorporating foreign nucleic acid, for selection and for transfer of the nucleic acid into a host cell. The gag, pol and env genes of suitable vectors also are known in the art. Thus, the relevant genes may be cloned into a selected vector and then used to transform the target cell of interest.

The env gene can be derived from any virus, including retroviruses. Examples of retroviral-derived env genes include, but are not limited to: gibbon ape leukemia virus (GaLV or GALV); Moloney murine leukemia virus (Mo-MuLV or MMLV), Harvey murine sarcoma virus (HaMuSV or HSV), murine mammary tumor virus (MuMTV or MMTV), human immunodeficiency virus (HIV) and Rous sarcoma virus (RSV). The env gene may encode an amphotropic envelope protein which allows transduction of cells of human and other species. Other env genes such as Vesicular stomatitis virus (VSV) protein G (VSV G), that of hepatitis viruses and of influenza also may be used.

It may be desirable to target the virus vector by linking the envelope protein with an antibody or a particular ligand for targeting the virus vector to antibody-producing cells (e.g., activated B-lymphocytes). Targeting may be accomplished by using an antigen-binding portion of an antibody or a recombinant antibody-type molecule, such as a single chain antibody, to target the retroviral vector to an antibody-producing cell.

The transgene can be any nucleic acid of interest which can be transcribed. Generally the transgene encodes a polypeptide. Preferably, expression of the polypeptide has some desirable effect. Transgenes of the virus vectors disclosed herein may include oncogenes and proto-oncogenes for transforming antibody-producing cells.

A transgene may be expressed from a promoter sequence present in the LTR region of the virus from which the virus vector is derived. Alternatively, the transgene may be expressed from another promoter sequence. The promoter sequence may be homologous or heterologous to the transgene sequence. A wide range of promoters may be utilized, including a viral or a mammalian promoter. Cell or tissue specific promoters can be utilized to target expression of gene sequences in specific cell populations. Preferably, the selected promoter expresses the transgene in antibody-producing cells.

Optionally, the nucleic acid of the virus vector contains a marker gene. Marker genes may be utilized to assay for the presence of the vector, and thus, to confirm infection and integration. The presence of a marker gene ensures the selection and growth of only those host cells which express the inserts. Genes for selecting or sorting may encode proteins that confer resistance to antibiotics and other toxic substances, e.g., histidinol, puromycin, hygromycin, neomycin, methotrexate, and cell surface or other markers (e.g., green fluorescent protein (GFP)).

The recombinant virus of the invention is capable of transferring a nucleic acid sequence into a mammalian cell. The term, "nucleic acid sequence", refers to any nucleic acid molecule, preferably DNA, as discussed in detail herein. The nucleic acid molecule may be derived from a variety of sources, including DNA, cDNA, synthetic DNA, RNA or combinations thereof. Such nucleic acid sequences may comprise genomic DNA which may or may not include naturally occurring introns. Moreover, such genomic DNA may be obtained in association with promoter regions, poly A sequences or other associated sequences. Genomic DNA may be extracted and purified from suitable cells. Alternatively, messenger RNA (mRNA) can be isolated from cells and used to produce cDNA by reverse transcription or other means.

The virus vectors are prepared by introducing the vector nucleic acid via transfection or infection into the packaging cell line. The packaging cell line produces vector viral particles that contain the vector nucleic acid (i.e., the transfer vector). The virus vector may be recovered from the culture media of the packaging cell line and titered by standard methods.

Stable cell lines where the packaging functions are configured to be expressed by a suitable packaging cell are known. For example, see Mann et al., Cell (1983), 133:153-165; and Ory et al., Proc. Natl. Acad. Sci. (1996) 93:11400 11406, which describe packaging cells.

Oncogenes and Proto-Oncogenes

The disclosed methods may include transfecting (e.g., by transducing or infecting) antibody-producing cells with one or more vectors (e.g., a virus vector) that express one or more oncogenes or proto-oncogenes. Subsequently, the antibody-producing cells may become transformed. In some embodiments of the disclosed methods, antigen-specific plasmacytomas develop subsequent to the expression of one or more oncogenes or proto-oncogenes in the transfected antibody-producing cells. Suitable oncogenes or proto-oncogenes for the present methods include those encoding c-myc, v-abl, Rb, p53, h-tert, v-fms, c-mos, mdm-2, p16/p19, v-ras, v-raf, and members of the bcl-2 family (e.g., bcl-xl). The preferred oncogenes or proto-oncogenes are those encoding c-myc, mouse c-myc, and v-abl. The oncogenes or proto-oncogenes may be expressed via an endogenous promoter for the oncogene or a heterologous promoter that effects expression of the oncogene or proto-oncogene in antibody-producing cells.

Screening and Selection for Immortalized Plasma Cells

After transfection (or transduction or infection), immortalized or transformed cells may be selected in vivo or ex vivo. In order to select for transformed cells in vitro (or ex vivo), the transfected cells may be grown and/or selected under conditions described herein for growing and/or selecting immunized cells. To select for transformed antibody cells ex vivo, the cells may be plated at approximately $1 \times 10^5$ per well in flat bottom microtiter plate. Individual wells can then be screened by ELISA for kappa-light chain containing antibodies and by FACS analysis to identify cells that produce antibody to the selected antigen. Antibody-secreting cells can be replated, screened again, and if still positive for IgG, the cells can be subcloned at least twice by limiting dilution. The stable subclones can then be grown further ex vivo or in vivo to generate antibody for characterization.

In order to select for transformed cells in vivo, the cells may be transferred to the peritoneal cavity of a mouse. Prior to transfer, the mouse optionally may have been primed with a suitable agent for inducing or enhancing production of ascitic fluid. After the cells are transferred, the mouse is monitored for production of ascitic fluid, which may be screened for the presence of antibody.

The presence of the antibodies produced by the methods disclosed herein may be determined by various assays. Assay techniques include but are not limited to immunofluorescence (IF) by cytofluorographic analysis or by cell sorting, indirect immunofluoroscence, immunoprecipitation, ELISA, agglutination and Western blot techniques.

ILLUSTRATIVE EMBODIMENTS

The following embodiments are illustrative and are not intended to limit the scope of the disclosed subject matter.

Embodiment 1

A method for producing immortalized antigen-specific plasma cells, comprising: a) contacting lymphocytes and an antigen to obtain immunized cells; b) selecting the immunized cells based on expression of CD138 or lack thereof; and c) contacting the selected cells with an activating agent to obtain activated lymphocytes; and d) immortalizing the activated lymphocytes, thereby producing the immortalized antigen-specific plasma cells.

Embodiment 2

The method of embodiment 1, wherein the method leads to a relative increase in the number of immortalized antigen-specific plasma cells produced by the method (e.g., about a 3-10 fold increase) as compared to methods in the prior art that do not include steps b) and/or c).

Embodiment 3

The method of embodiment 1 or 2, wherein step d) comprises fusing the activated lymphocytes and myeloma cells to obtain hybridoma cells.

Embodiment 4

The method of embodiment 1 or 2, wherein step d) comprises transfecting the activated lymphocytes with a viral vector that transforms the transfected cells to obtain plasmacytoma cells.

Embodiment 5

The method of embodiment 4, wherein transfecting comprises infecting the activated lymphocytes with the viral vector and the viral vector comprises one or more oncogenes.

Embodiment 6

The method of any of embodiments 1-5, further comprising growing the immortalized antigen-specific plasma cells to obtain antibodies that specifically bind to the antigen.

Embodiment 7

The method of any of embodiments 1-6, further comprising growing the activated lymphocytes in the presence of the activating agent.

Embodiment 8

The method of embodiment 7, wherein the activating agent comprises a cytokine or an antibody (e.g., an antibody against CD40 or IgM).

Embodiment 9

The method of embodiment 8, wherein the cytokine comprises IL-4.

Embodiment 10

The method of embodiment 7, wherein the activating agent comprises the antigen (and optionally the activating agent comprises cells selected from the group consisting of antigen-specific T cells, dendritic cells, macrophage cells, and combinations thereof).

Embodiment 11

The method of embodiment 7, wherein the activated lymphocytes are grown in the presence of the activating agent for at least about 1-4 days.

Embodiment 12

The method any of embodiments 1-11, wherein the lymphocytes comprise splenocytes.

Embodiment 13

The method of any of embodiments 1-12, wherein selecting comprises depleting the immunized cells of CD138-positive cells.

Embodiment 14

The method of embodiment 3, wherein the method is performed entirely in vitro.

Embodiment 15

The method of embodiment 4, wherein the method is performed entirely in vitro.

Embodiment 16

The method of claim 3, further comprising growing the hybridoma cells to obtain monoclonal antibodies that specifically bind to the antigen.

Embodiment 17

The method of claim 4, further comprising growing the plasmacytoma cells to obtain monoclonal antibodies that specifically bind to the antigen.

Embodiment 18

A method for producing monoclonal antibodies comprising: a) contacting lymphocytes and an antigen to obtain immunized cells; b) selecting the immunized cells based on expression of CD138 or lack thereof; c) contacting the selected cells with an activating agent to obtain activated lymphocytes; d) immortalizing the activated lymphocytes, thereby producing immortalized antigen-specific plasma cells; and e) culturing the immortalized antigen-specific plasma cells to produce the monoclonal antibodies.

Embodiment 19

The method of embodiment 18, wherein step c) comprises fusing the activated lymphocytes and a myeloma cell to obtain hybridoma cells.

Embodiment 20

The method of embodiment 18, wherein step c) comprises transfecting the activated lymphocytes with a viral vector that transforms the transfected cells to obtain plasmacytoma cells.

EXAMPLES

The following examples are illustrative and are not intended to limit the disclosed subject matter.

Example 1

Method for Plasmacytoma Development In Vivo or In Vitro

Figure 2:
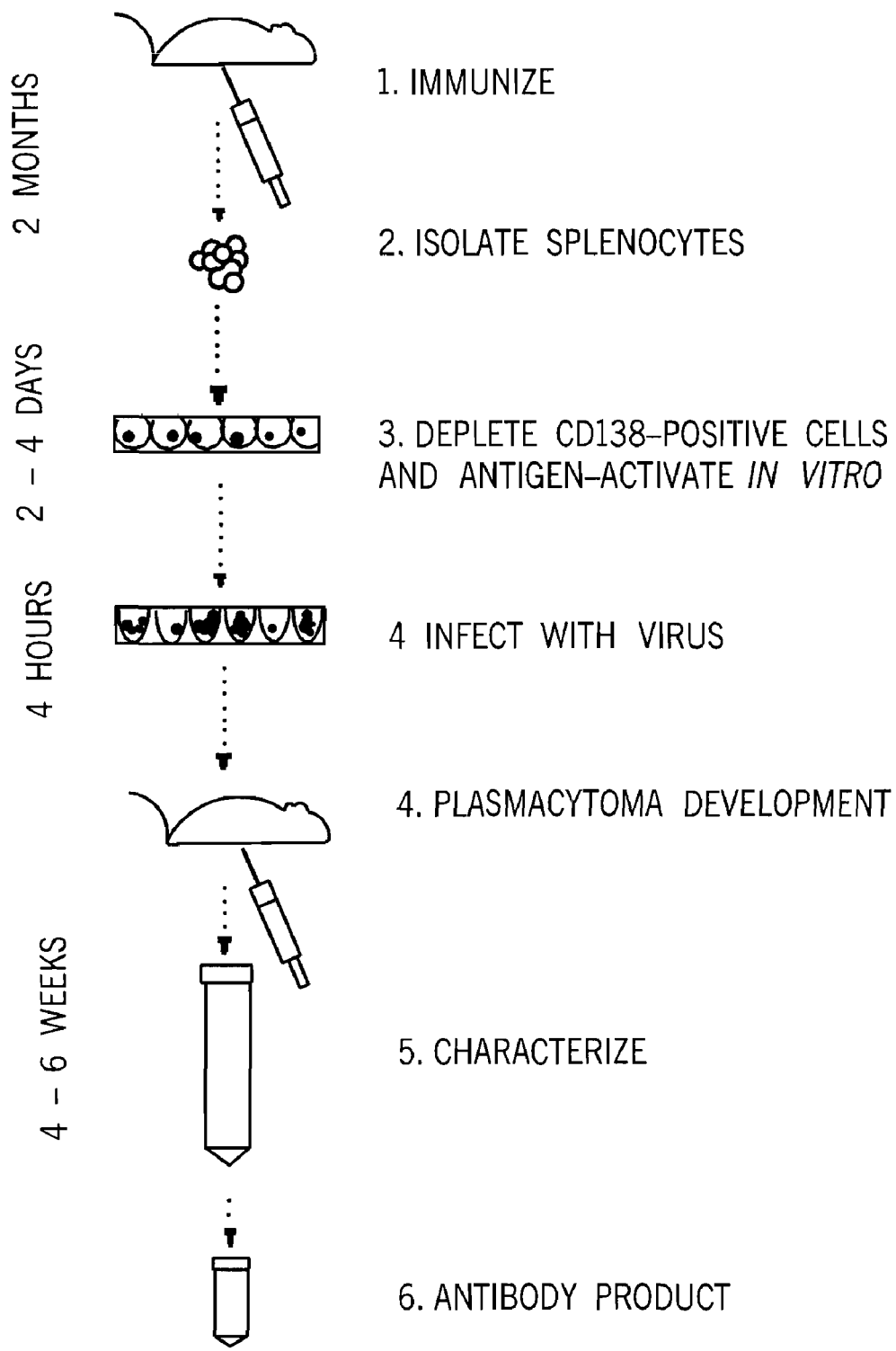
FIG. 2 is an exemplary method for producing monoclonal antibodies that includes in vitro stimulation of a lymphocyte population depleted of CD138 plamsmablasts and in vivo plasmacytoma development.
Figure 3:
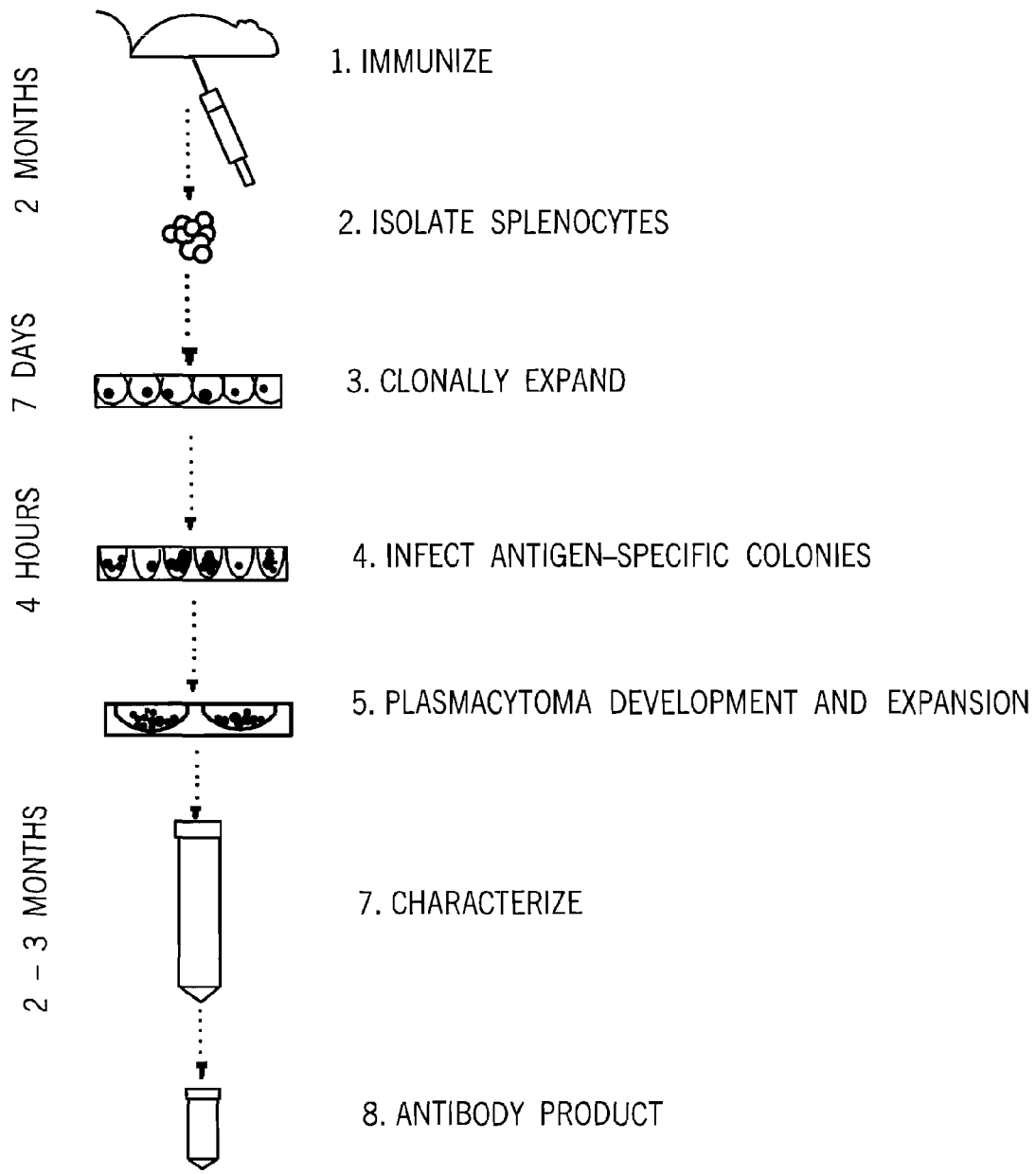
FIG. 3 is an exemplary method for producing monoclonal antibodies that includes in vitro plasmacytoma development.

FIGS. 1-3 outline exemplary methods for producing monoclonal antibodies. In the method of FIG. 3, B cells from immunized mice are clonally expanded for several days to induce differentiation and Ig secretion. Colonies that secrete Ig against the immunizing antigen are infected with a ABL-MYC retrovirus and then culture in vitro for plasmacytoma development and expansion.

Example 2

Transformation of CD138-Enriched Cells by ABL-MYC Retrovirus

Splenocytes isolated from mice immunized with the α-subunit of *E. coli* RNA polymerase were fractionated with an anti-CD138 antibody conjugated to phycoerythrin (PE) and anti-PE magnetic beads (FIG. 4). Evaluation of the populations by flow cytometry revealed that the magnetically labeled population (CD138-enriched) contained cells that were stained strongly with antibodies directed against the plasma cell marker CD138. These same cells exhibited high to low staining with antibodies directed against the B cell lineage marker B220. Furthermore, Ag-specific ELISPOT data indicated that Ag-specific, IgG secreting cells were enriched more than ten-fold in the CD138-enriched population when compared to non-fractionated splenocytes (total splenocytes). These data indicate that the magnetically labeled cells were enriched for plasmablasts and plasma cells. The non-labeled cells (CD138-depleted) showed an ~50% reduction of plasmablasts and plasma cells by flow cytometry and ELISPOT.

Total splenocytes, CD138-enriched, and CD138-depleted populations were infected with ABL-MYC retrovirus and injected into recipient mice. Only $1.5 \times 10^5$ CD138-enriched cells were injected per mouse, while total splenocytes and CD138-depleted cells were injected at $2.5 \times 10^6$ cells per mouse. Each cell population was injected with $2.5 \times 10^6$ non-infected splenocyte carriers per mouse isolated from a green fluorescent protein (GFP)-immunized mouse.

TABLE 1

Magnetically enriched $CD138^{high}$ cells are transformed into Ag-specific plasmacytomas by ABL-MYC infection.

| mouse ID | Total splenocytes | | | | | | CD138-enriched | | |
|---|---|---|---|---|---|---|---|---|---|
| | 893A | 893B | 893C | 893D | 893E | 893F | 894A | 894B | 894C |
| latency (days) | 60 | 30 | 52 | 36 | 46 | 36 | 32 | 30 | 42 |
| volume of ascites (mL) | 1.0 | 3.0 | 3.0 | 2.4 | 3.0 | 1.9 | 1.9 | 3.3 | 2.4 |
| Ag-specific titer | 22500 | 1010 | 2400 | 1480 | 2000 | 3000 | 2100 | 2800 | 480 |
| GFP (+/− at 1/100) | − | − | − | − | − | − | − | − | − |
| ABL-MYC integration | + | + | + | + | + | + | + | + | + |

TABLE 1-continued

Magnetically enriched CD138$^{high}$ cells are transformed into Ag-specific plasmacytomas by ABL-MYC infection.

|  | CD138-enriched | | | CD138-depleted | | | | | |
| --- | --- | --- | --- | --- | --- | --- | --- | --- | --- |
| mouse ID | 894D | 894E | 894F | 895A | 895B | 895C | 895D | 895E | 895F |
| latency (days) | 38 | Sac 60 | 32 | 38 | 52 | 38 | 36 | 52 | 38 |
| volume of ascites (mL) | 3.0 | NA | 3.2 | 0.5 | 0.9 | 1.5 | 1.0 | 1.8 | <0.1 |
| Ag-specific titer | 27000 | \| | 837 | 469 | 850 | 702 | 926 | nt | nt |
| GFP (+/− at 1/100) | − | \| | − | − | − | − | − | − | nd |
| ABL-MYC integration | + | ⊥ | + | + | + | + | + | + | + |

In Table 1, the indicated cell fractions were infected with ABL-MYC, washed, and injected into six recipient mice along with non-infected splenocyte carriers isolated from GFP-immunized mice. Ascites were collected from all mice, except 894E, which did not develop ascites within 60 days and was sacrificed. Latency is the time required for ascites development from the time of injection. Ag-specific titer was calculated by α-core-specific ELISA and is defined as the dilution that gives half-maximal absorbance. GFP-specific ELISA was carried out at a single dilution of 1:100. A negative equals an absorbance less than twice background. ABL-MYC integration was carried out as described herein. A positive indicates a clearly visible PCR band upon electrophoretic separation and staining. "NT" means "no titer." "ND" means "not determined."

Table 1 shows that all but one of the recipient mice injected with CD138-enriched cells developed ascites containing Ag-specific IgG. Furthermore, the cells contained within the ascites were found to have the ABL-MYC provirus integrated into the cellular DNA. Table 1 also shows that the infected CD138-depleted cells developed ascites with 4 of 6 ascites containing Ag-specific IgG. Ascites developed from infected CD138-depleted cells may be due to the incomplete depletion of CD138$^{high}$ cells or, alternatively, due to transformation of CD138$^{low}$ cells.

Example 3

Splenocytes Up-regulate CD138 in Response to Anti-CD40 and Cytokines

Figure 5A:
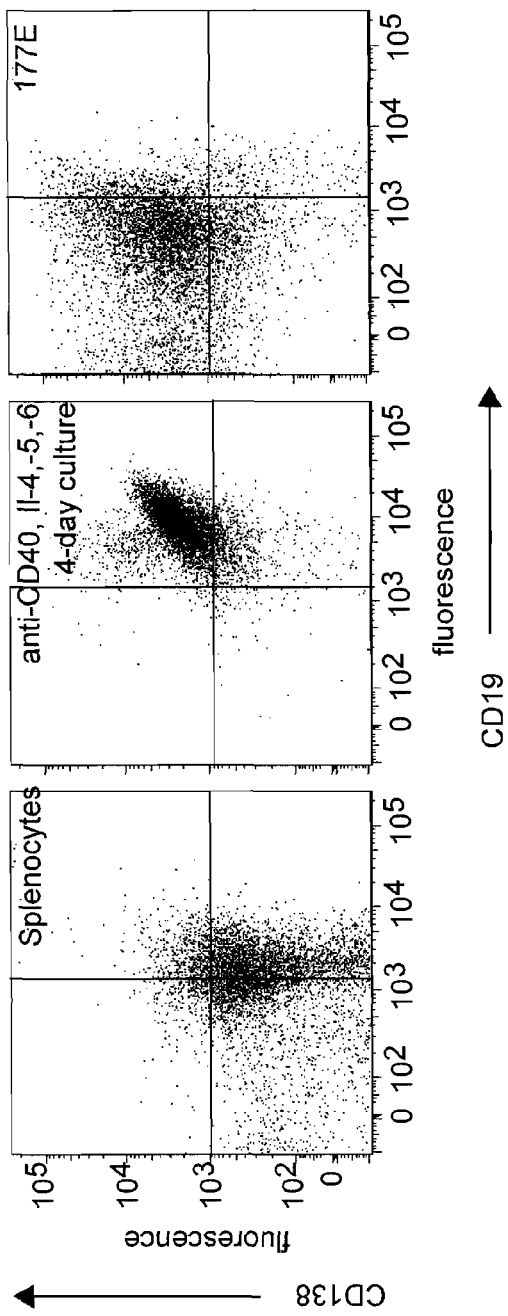
FIG. 5 demonstrates murine splenocyte upregulation of CD138 in response to anti-CD40 and interleukins 4, 5, and 6. Splenocytes were cultured in the presence of 1 µg/mL anti-CD140, 150 ng/mL IL-4, 10 ng/mL IL-15, and 10 ng/mL IL-6. After 4 days, cells were collected and stained with APC-Cy7-labeled anti-CD45, PE-Cy5.5-labeled anti-CD19, PE-labeled anti-CD138, FITC-labeled anti-CD3, and APC-labeled anti-F4/80 and anti-CD11b before analysis by flow cytometry. A. CD19 and CD138 expression profiles of freshly isolated splenocytes, the stimulated 4-day culture, and plasmacytoma line 177E. Cells shown were gated for single cells and CD45 (lymphocytes)-positive cells. Cells expressing CD3 (T-cells) and F4/80/CD11b (macrophages) were excluded from the analysis. B. Histogram of CD138 expression for the samples shown in A. Plasmacytoma line 177E is an ABL-MYC-transformed line developed and isolated from mouse ascites fluid.
Figure 5B:
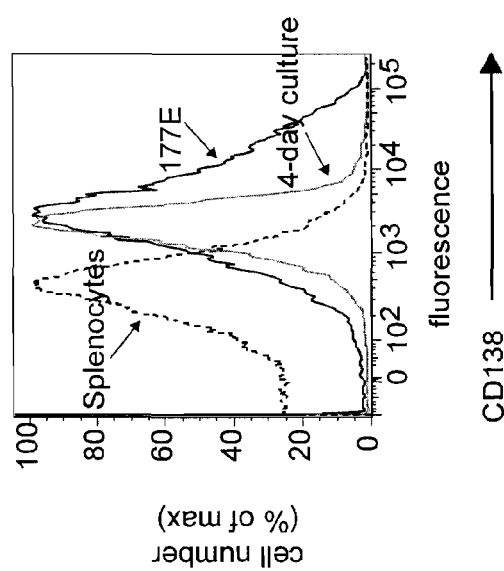

Splenocytes were harvested from immunized mice and cultured with a mAb against CD40 and IL-4, IL-5, and IL-6 for 4 days. Cells were then collected and stained for flow cytometry analysis with antibodies against CD45 (panlymphocyte marker), CD3 (T cell marker), F4/80 and CD11b (macrophage/monocyte markers), CD19 (B cell lineage marker), and CD138 (plasma cell marker) (FIG. 5). As controls, freshly isolated murine splenocytes (negative) and the ABL-MYC-transformed plasma cell line 177E (positive) were used. Compared to freshly isolated splenocytes, the 4-day culture exhibited a marked increase in both CD19 (B cell lineage) and CD138 (plasma cell) fluorescence signal intensity. The fully transformed plasma cell line 177E is CD19$^{low}$/CD138$^{high}$, as expected for a plasma cell line. These results indicate that in vitro culture systems may be used to activate and differentiate splenocytes into the cell types needed for plasmacytoma development.

Example 4

Isolation of ABL-MYC Transformed Plasmacytomas Upon Infection of In Vitro Differentiated Splenocytes Splenocytes were cultured as described in Example 3 and FIG. 5 and infected with ABL-MYC before plating onto γ-irradiated OP-9 feeders in the presence of 10 ng/mL interleukin (IL)-6. Two cell lines were isolated from primary cultures at days 21 (designated C1) and 45 (C2) and further propagated on OP-9 feeders. After two (C2) and three (C1) passages, cells were collected and stained for flow cytometry as described in Example 3, FIG. 5. Both cell lines were found to exhibit high CD138 expression and low CD19 expression as expected for a plasma cell line (FIGS. 6A and B). In addition, both cell lines had the ABL-MYC viral gene integrated into their genome (FIG. 6C). Both cell lines secreted IgG into the media (FIG. 6D). These results indicate that ABL-MYC dependent, transformed plasmacytoma lines can be isolated from in vitro cultures.

Example 5

Cell Determinate Labeling and FACS

Naïve and memory B cells, plasmablasts and plasma cells can be distinguished by the expression of cell surface markers (Table 2). Because CD138$^{high}$ cells may be the target of ABL-MYC transformation (see Table 1), CD138$^{low}$/B220$^{high}$ naïve and memory cells may be separated from CD138$^{high}$/B220$^{intermediate}$ plasmablasts and CD138$^{high}$/B220$^{low}$ plasma cells. Optionally, plasmablasts and plasma cells can be separated based on B220 expression or naïve and memory B cells can be separated based on IgD expression.

TABLE 2

B lineage cell surface determinant markers

| B cell type | Surface markers |
| --- | --- |
| Naïve | B220$^{high}$, IgD$^{high}$, CD138$^{low}$ |
| Memory | B220$^{high}$, IgD$^{low}$, CD138$^{low}$ |
| Plasmablast | B220$^{intermediate}$, IgD$^{low}$, CD138$^{high}$ |
| Plasma | B220$^{low}$, IgD$^{low}$, CD138$^{high}$ |

Splenocytes isolated from immunized mice can be labeled with fluorophore-conjugated mAbs directed against the cell surface markers (Tables 2 and 3) using standard protocols for cytometry staining. Plasma cells were observed not to express high levels of B200 or CD19.

TABLE 3

Fluorophore-conjugated mAbs for analysis of lymphocytes.

| Marker | Cell identifier | Fluorophore | mAb clone |
|---|---|---|---|
| B220 | B cell lineage | APC-Cy5.5 | RA3-6B2[b] |
| IgD | Naive B cell | FITC | 11-26c (11-26)[b] |
| CD138 | Plasmablast, plasma | PE | 281-2[a] |
| CD19 | B cell lineage | PE-Cy5.5 | 6D5[b] |
| CD3e | T cell | PE-Cy5, FITC | 145-2C11[a] |
| CD11b | Monocyte/macrophage | PE-Cy7, FITC | M1/70[b] |

[a]BD Biosciences (San Jose, CA); [b]eBioscience (San Diego, CA).

Live, labeled cells may be sorted on a BD FAC-SVantage SE equipped with the FACSDiVa digital electronics package. Cells will be sorted into cooled collection tubes containing fetal calf serum (FCS). Confirmation of sorting and assessment of purity may be carried out by running a small fraction of the sorted populations on a BD LSRII benchtop cytometer. In addition to cells that express $CD138^{high}$ or $B220^{high}$, cells that are neither $CD138^{high}$ nor $B220^{high}$ may be collected as well. Sorted populations may be tested for total and Ag-specific Ig secretion by ELISPOT. FIG. 4 shows an example of Ag-specific ELISPOT.

Example 6

ABL-MYC Infection

Sorted populations are centrifuged, washed, and resuspended to $4 \times 10^6$ cells per mL in infection media (RPMI 1640 supplemented with 100 U/mL penicillin/streptomycin, 2 mM L-glutamine, 50 μMβ-mercaptoethanol and 20% FCS). The cells are combined with an equal volume of ABL-MYC virus and incubated at 37° C. for 4 h in 5% $CO_2$. Cells will be washed 3 times in phosphate buffered saline (PBS).

Example 7

Transplantation and Ascites Development

Cells are injected intraperitoneally into BALB/c female recipient mice. The recipient mice are primed with 0.5 mL of pristane 7-10 days before receiving infected cells. Upon injection, infected cells are incubated for up to 60 days with typical ascites development occurring within 30-45 days. Ascites fluid and cells are collected upon development for analysis.

The total number of sorted, infected cells injected per recipient mouse may depend upon the population sorted, the efficiency of the sorting, and the recovery of viable, sorted cells. Typically, $CD138^{high}$ cells represents 1-4% of the total splenocyte population (See FIG. 4, total splenocytes). The sorting of $10^8$ cells may theoretically yield a maximum 1-3× $10^6$ $CD138^{high}$ cells, but the yield may be lower due to cell death during the sort. Therefore, cells may be injected based on the number of cells present in unsorted splenocytes. For example, a population of $5 \times 10^6$ total, infected splenocytes per mouse for ascites development, may be estimated to contain 5 to $15 \times 10^4$ $CD138^{high}$ cells. For sorted $CD138^{high}$ cells, 5 to $15 \times 10^4$ cells may be injected per recipient mouse depending on cell recovery.

In some processes, infected splenocytes may be injected into recipient mice with-out separating cell types. B-lymphocytes may be injected together with T-lymphocytes and monocytes/macrophages. To approximate a typical microenvironment, sorted ABL-MYC infected populations may be injected into recipient mice along with non-infected splenocytes ($2.5 \times 10^6$ per mouse). These "carrier" splenocytes may be isolated from mice immunized with a different antigen to differentiate the Ag-specificity of the infected and non-infected cells as well as to monitor viral carry-over and transformation of the carrier splenocytes. Viral carry-over can be tested by Ag-specific ELISA of developed ascites fluid using plates coated with the two different antigens.

Example 8

Analysis of Ascites

Ascites fluid generated may be titered for Ag-specific Ig by ELISA and tested for total Ig production. DNA may be purified from ascites cells and tested for integration of the ABL-MYC provirus into the cell genome. The cell population that is targeted by ABL-MYC may be expected to develop ascites in recipient mice within 60 days, producing plasmacytomas containing integrated ABL-MYC and secreting Ag-specific Ig.

Example 9

Mouse Immunization and Splenocyte Isolation

The recombinant α-subunit of *E. coli* RNA polymerase may be used as an exemplary antigen for primary mouse immunizations. Mice may be immunized with the α-subunit by intraperitoneal and subcutaneous injections with 50% of the protein injected at each location. An exemplary immunization protocol is described in Table 4. Mice may be final boosted 14-28 days following the second boost.

TABLE 4

Exemplary Immunization Protocol

| Immunization (per mouse) | Day | Protein | Adjuvants |
|---|---|---|---|
| Initial | 0 | 10 μg | Freund's Complete |
| First boost | 14 | 20 μg | Freund's Incomplete |
| Second boost | 28 | 40 μg | Freund's Incomplete |
| Final boost | 42-56 | 120 μg | PBS |

Test bleeds (75 μL taken on days 0, 28, and 42) may be used to determine the immunogenic response of the mice to the antigen by ELISA. Mice with an OD of 10 times greater than background at a test bleed 2 sera dilution of 1:1,000 may be used for final boosts and experiments.

For non-infected "carrier" splenocytes described above, mice may be immunized with GFP instead of the a subunit of *E. coli* RNA polymerase.

Spleens from immunized mice may be harvested 4 days after the final boost. Single-cell suspensions may be made by perfusing the spleens with 20 mL of infection media per spleen. Red blood cells may be lysed using Red Blood Cell Lysing Buffer (Sigma, St. Louis, Mo.) before resuspending in the appropriate cell media.

Example 10

Cell Counting

Cell recovery and viability following splenocyte isolation, cell sorting, infection, and ascites development may be

Example 11

ELISA

For Ag-specific ELISA, 100 ng/well antigen may be coated on a 96-well plate and then blocked with PBS containing 1% milk. Serial dilutions (1:100 to 1:12800) of mouse sera or ascites fluid may be incubated on the coated and blocked plates, and then washed with 0.1% Tween-20 in PBS (PBSST). A secondary goat anti-mouse heavy and light chain mAb conjugated to horseradish peroxidase (HRP) may be used for detection. After washings, the signal may be detected using tetramethylbenzidine liquid substrate (Sigma), stopped by the addition of 1 $NH_2SO_4$, and read at 450 nm on an ELISA plate reader from Molecular Devices (Sunnyvale, Calif.).

Total IgG testing of ascites fluid may be carried out using the Easy-titer Mouse IgG Assay Kit (Pierce, Rockford, Ill.).

Example 12

ELISPOT

Ninety-six (96)-well PVDF plates (MSIPS4510; Millipore) may be hydrated with 70% ethanol and washed with PBS. Plates then may be coated overnight with 500 ng antigen in 100 µL per well in PBS. After a single PBS wash, plates may be blocked with cell media for at least 2 h at 37° C. before decanting. Cells may be serially diluted in media and aliquoted in duplicate onto the plate at 100 µL of cells per well. After 5 h at 37° C. in 5% $CO_2$, plates may be washed twice with PBS and four times with PBSST. To detect bound IgG, a 1:5000 dilution in cell media of anti-mouse IgG HRP (Sigma) may be added at 80 µL per well and incubated at 4° C. overnight. Plates may be washed 3 times with PBSST followed by 3 washes with PBS. Spots may be developed by the addition of AEC reagent (BD Biosciences) at 100 µL per well and incubated for 5-6 minutes with visual monitoring. Color development may be stopped by extensive washing with tap water. Plate backing may be removed and plates allowed to dry overnight in the dark. Spot imaging and analysis may be carried out by ZellNet Consulting (Fort Lee, N.J.).

Example 13

ABL-MYC Integration

DNA from cells may be isolated using the Qiagen DNeasy kit. PCR amplification may be performed with Roche's PCR Core Kit (Basel, Switzerland). Primers may extend from the 3'-end of the v-abl gene to the 5'-end the c-myc gene and include both intervening DNA sequences and the TK promoter used for murine c-MYC expression. This method may enable detection only of integrated proviral DNA where no DNA from endogenous abl or myc sequences is amplified.

Example 14

E14-B5 System and Bulk Culture Optimization

The cell line EL4-B5 is a subclone of murine EL4 thymoma that is a bromo-deoxyuridine-resistant mutant. EL4-B5 is grown with B cells to activate the B cells via direct cell contact to induce proliferation, differentiation, and secretion of Ig.

Cultures may be seeded on 24-well plates in EL4-B5 media (RPMI 1640 supplemented with 100 U/mL penicillin/streptomycin, 2 mM L-glutamine, 50 µM β-mercaptoethanol, 2 mM HEPES and 10% FCS) along with conditioned media (see below). B cells (50,000) and irradiated EL4-B5 cells (250,000) may be added to each well in 1 mL. Cultures may be fed every 3 days by removing 0.5 mL of old media and adding 0.5 mL of fresh media (with conditioned media supplements).

Cultures may be harvested at 2-day intervals for 8 days. Culture media may be tested for total IgG, IgM, and IgA production to determine the total amount of Ig secreted and the extent of Ig class switching. Cells may be stained for cell determinate markers and analyzed by flow cytometry to determine the developmental state of the expanded B cells.

Example 15

Cytokines and Conditioned Media

Cytokines may be obtained as purified proteins or from culture supernatants of activated T cell and macrophage cultures. For human B cells, a cocktail of recombinant human IL-1β, TNFα, IL-2 and IL-10 may be sufficient for maximum B cell proliferation and Ig secretion. Conditioned media from phorbol 12-myristate 13-acetate (PMA)-stimulated EL4-B5 cells, UV stimulated PD3188 (macrophage) cells or phytohemagglutinin (PHA)/PMA-stimulated human T-cell and macrophage co-cultures may be used to support murine B cell proliferation and Ig secretion.

To define the best conditions for B cell proliferation, Ig secretion, and differentiation, different combinations of conditioned media may be tested, including conditioned media from PMA/PHA-stimulated EL4-B5 cells, PMA/PHA-stimulated P388D1 (IL-1) cells and PMA/PHA-stimulated co-cultures of EL4-B5 and P388D1 (IL-1) cells. Condition media may be tested by supplementing EL4-B5 media with 0, 5, 10, or 20% conditioned media. For each condition, B cells may be cultured as described above in multiple wells of 24-well plates. Cultures may be harvested every two days and tested for Ig secretion, Ig class switching, and B cell differentiation as described above.

Example 16

Single-Assay Cultures for Ag-Specific B Cell Expansion

Cultures may be propagated in 96-well plates in EL4-B5 media supplemented with the optimized conditioned media. Irradiated EL4-B5 cells (50,000) may be added to each well along with one B cell (mean per well) in 100 µL total volume. Cultures may be fed every two days by replacing 50% of the media with fresh media. Cultures may be tested at day 8 for Ag-specific Ig, at which point the cultures containing Ag-specific Ig may be infected for plasmacytoma development.

Example 17

Ag-Specific B Cell Enrichment

The total number of Ag-specific B cells isolated from the spleen of an immunized mouse may be less than 2% of the total splenocyte population. Enrichment for Ag-specific B cells may be performed in at least two ways. One way is to positively select for Ag-specific cells using the antigen itself. This may be achieved by panning against antigen-coated plates, using a combination of labeled antigen and magnetic beads, or by FACS using cells incubated with fluorescently labeled antigen. An alternative may be to negatively select for Ag-specific cells. This may be done by using antibodies against non-B cells and non-Ag-specific cells and magnetically removing those cells.

To increase the frequency of clonally expanded Ag-specific B cells in single cell cultures, we will use cell surface determinate labeling and magnetic depletion of non-B cell and non-Ag-specific B cells to increase the frequency of Ag-specific B cells. T-cells and monocytes/macrophages will be labeled with anti-CD3e and anti-CD11b mAbs conjugated to fluorescein isothiocyanate (FITC) (Table 3). In addition, naïve B cells may be labeled with an anti-IgD mAb conjugated to FITC. Labeled cells may be magnetically depleted using Easy-Sep Mouse FITC Selection Kit (StemCell Technologies). Confirmation of separation may be confirmed by flow cytometry and depletion conditions may be optimized, if necessary, by adjusting the amount of antibody used to label cells. The non-labeled cells may be clonally expanded as described above and the frequency of clonally expanded Ag-specific B cells may be compared to cultures of total splenocytes.

Example 18

Culturing and Conditioned Media

EL4-B5 cells may be grown in EL4-B5 media maintaining a cell density of less than $5 \times 10^5$ cells per mL. To stop growth, EL4-B5 cells may be γ-irradiated at 5000 rad. Irradiated cells then may be centrifuged, resuspended in EL4-B5 media supplemented with 10% DMSO, and frozen in liquid nitrogen. Adherent P388D1 (IL-1) (ATCC, Manassas, Va.) cells may be grown in RPMI 1640 supplemented with 2 mM L-glutamine, 1.5 g/L sodium bicarbonate, 4.5 g/L glucose, 10 mM HEPES, 1 mM sodium pyruvate, and 10% FCS. Subcultures may be prepared by scraping and subcultivating at a ratio of 1:4.

Conditioned media may be prepared by culturing EL4-B5 and/or P388D1 (IL-1) cells at $5 \times 10^5$ cellsper mL in EL4-B5 media supplemented with 5 μg/mL PHA (Sigma, L-8902) and 10 ng/mL PMA (Sigma, P-8139). After no more than 36 hours, cells may be removed by centrifugation, and the supernatant may be harvested before filtering through a 0.2 pm filter. The conditioned media may be stored in aliquots at −80° C. until needed.

Example 19

Ig Quantification

Total IgG, IgA, and IgM quantification of tissue culture supernatants may be carried out using Bethyl Laboratories (Montgomery, Tex.) Ig ELISA Quantification Kits according to the manufacture's directions.

Example 20

Infection and Transformation of Cultured B Cells with ABL-MYC

B cells which have been differentiated and expanded in bulk cultures are tested to determine whether they can be infected and transformed by ABL MYC. B cells may be cultured in the EL4-B5 system for the number of days required to obtain the proper level of differentiation for efficient infection and transformation.

The infected cells are injected into mice along with non-infected splenocyte carriers to ensure a suitable microenvironment for plasmacytoma development. Successful infection and transformation may be judged by one or more of: (1) the development of ascites within a suitable time frame (60 days); (2) ABL-MYC integration into DNA isolated from ascites cells; and (3) the presence of Ig in ascites fluid.

Example 21

ABL-MYC Transformation Efficiency

Using single-cell culturing conditions described herein, clonally expanded B cells are infected with ABL-MYC and the efficiency of transformation is determined. Transformation of B cells may be determined in at least two ways: (1) by continued in vitro culturing; and, (2) by injecting the infected cells into recipient mice. Clonally expanded, Ag-specific B cells may be infected by the addition of ABL-MYC virus directly to each well of the microplate at 50% of the total volume (i.e., 50 μL media plus 50 μL virus pool). After 4 hours at 37° C., 100 μL of media is added to each well and the plate is centrifuged at 500×g for 10 min in an Allegra 25R Beckman Centrifuge with a 96-well plate adaptor. Approximately, 100 μL of media is removed and the wash step is repeated two more times.

For in vitro transformation, infected cells are washed three times. Cells from each well are transferred and expanded into a well of a 24-well plate for plasmacytoma development. Irradiated EL4-B5 cells (250,000) are added to each well along with 1 mL of the cell media (containing optimized conditioned media as described herein). Cells re fed every 3 days by replacing 50% of the media for up to 60 days. Cultures are visually inspected every 2-3 days for expansion of transformed cells. Upon transformation, cell supernatant is tested for Ag-specific and total Ig secretion and DNA is extracted from cells to confirm ABL-MYC integration.

The infected cells also may be grown in the presence of irradiated stromal feeders such as OP-9 cells. The infected cells also may be grown in the presence of other media supplements, such as ascites fluid generated by the injection of the SP2/0 myeloma cells into pristane-primed mice or specific cytokines such as IL-6.

For injection into pristane-primed mice, the cells in each well are resuspended in PBS and transferred to a 15 mL conical tube containing 10 mL PBS. Non-infected "carrier" splenocytes ($2.5 \times 10^6$) are added to each tube immediately before centrifuging at 3000×g for 10 min. Cells are resuspended in 0.5 mL PBS and injected intraperitoneally into recipient mice for ascites development. Mice are incubated for up to 90 days and developed ascites are collected. Ascites fluid is tested for Ag-specific and total Ig. Ascites cells also is tested for DNA integration of viral ABL-MYC. Transformation efficiency is measured by the number of ABL-MYC-dependent ascites developed as a function of colonies infected and injected. Transformation efficiency is measured on a per colony basis.

Example 22

CD138-Depleted Splenocytes Activated In Vitro to Produce Plasmablasts in Response to Antigen Splenocytes isolated from mice immunized with the α-subunit of *E. coli* RNA polymerase (Ag) were magnetically depleted of CD138-positive cells using an anti-CD138 antibody conjugated to PE and StemCell Technologies EasySep PE-selection kit. Depleted cells ($5 \times 10^6$ cells/mL) were activated for 2 (day 2) or 4 (day 4) days in the presence of 20 ng/mL interleukin 4 along with 0, 10 or 500 ng/mL Ag. FIG. 7 shows the expression profile for B220 and CD138 is shown for parental splenocytes before and after magnetic depletion. Cells were stained with fluorophore-conjugated antibodies against the cell-determinant surface antigens CD45 (lymphocytes), B220 (B cells), CD138 (plasmablasts), CD11b (monocytes/macrophages) and CD3e (T cells) before analysis on a Beckman LSRII benchtop cytometer. Data is not shown for CD45-negative, CD3e-positive and CD11b-positive cells. Because of B220 and CD138 expression drift, possibly due to tissue culture adaptation, the percentage of CD138-positive cells were not analyzed for the day 4 cultures. These results show that splenocytes depleted of CD138-positive cells (i.e., plasmablasts, a target of ABL-MYC virus) can be activated in vitro to produce plasmablasts (new targets) in an antigen-dependent manner.

Example 23

Figure 8:
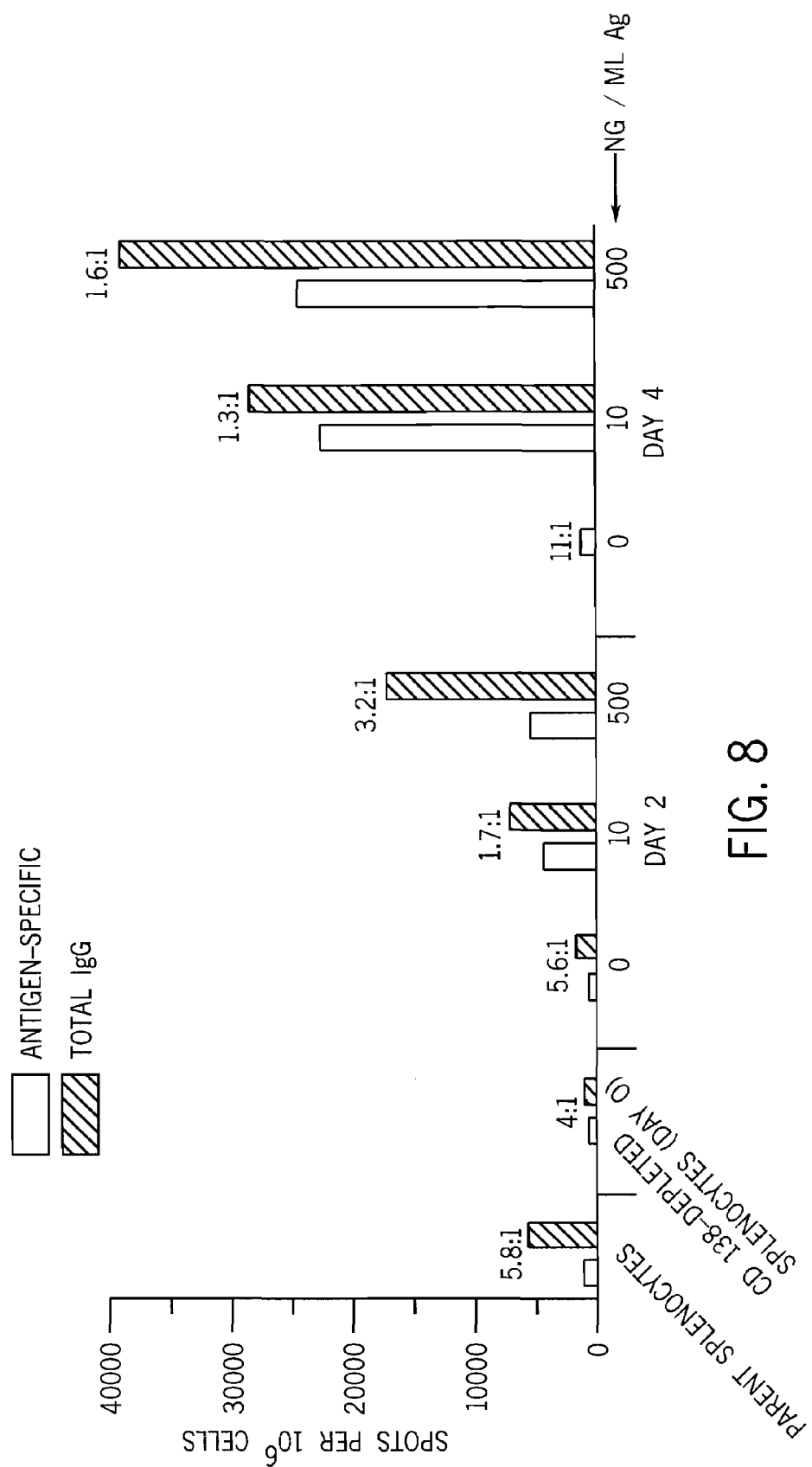
FIG. 8 demonstrates in vitro activation of CD138-depleted splenocytes with antigen results in the secretion of antigen-specific IgG. Control (Parental) splenocytes, CD138-depleted cells and activated day 2 and day 4 cultures described in Example 22, FIG. 7 were serially diluted and analyzed for antigen-specific (open bars) and total (closed bars) IgG secretion by ELISPOT. Spots developed were counted manually on a dissection microscope. The ratio of total IgG spots to antigen-specific spots (i.e., non-specific to antigen-specific) is indicated above the bars for each cell condition.

In Vitro Activation of CD138-Depleted Splenocytes with Antigen Results in the Secretion of Ag-Specific IgG Parental splenocytes, CD138-depleted cells and activated day 2 and day 4 cultures described in Example 22, and FIG. 7 were serially diluted and analyzed for antigen-specific and total IgG secretion by ELISPOT (FIG. 8). Spots developed were counted manually on a dissection microscope. The ratio of total IgG spots to antigen-specific spots (i.e., non-specific to antigen-specific) is indicated above the bars for each cell condition. These results show that the plasmablasts generated after two or four days of activation in the presence of antigen secrete IgG and that the IgG response is primarily antigen-specific. The fraction of cells secreting IgG is much higher for the antigen-activated day 2 and day 4 cultures when compared to those cultured in absence of antigen or even the parental splenocytes. In addition, the ratio of non-specific to antigen-specific IgG secreting cells is much lower for the in vitro activated cells.

Example 24

In Vitro Activation of CD138-Depleted Splenocytes with Antigen Results in a Higher Probability of Developing Ag-Specific Plasmacytomas and Ascites Cells activated in vitro (FIG. 8) will be infected with ABL-MYC for four hours before injection into recipient mice. The mice will be allow to incubate for up to 75 days for antigen-specific plasmacytoma and ascites development. The higher ratio of antigen-specific secreting splenocytes after activation of CD138-depleted splenocyte may result in an overall increase in the number of antigens specific plasmacytomas that develop when the cells are injected intraperitoneally into BALB/c female recipient mice. The recipient mice are primed with 0.5 mL of pristane 7-10 days before receiving infected cells. Ascites fluid and cells are collected upon development for analysis.

To approximate a typical microenvironment, in vitro activated and ABL-MYC infected populations may be injected into recipient mice along with non-infected splenocytes ($2.5 \times 10^6$ per mouse). These "carrier" splenocytes may be isolated from mice immunized with a different antigen to differentiate the Ag-specificity of the infected and non-infected cells as well as to monitor viral carry-over and transformation of the carrier splenocytes. Viral carry-over can be tested by Ag-specific ELISA of developed ascites fluid using plates coated with the two different antigens.

Example 25

CD138-Depleted, In Vitro Activated Lymphocytes Form Antigen-Specific Hybridomas More Efficiently than Untreated Lymphocytes Splenocytes from α-core immunized mice were CD138-depleted and in vitro activated with 10 ng/ml antigen for three days as described in Example 23. Activated lymphocytes were counted and $26.2 \times 10^6$ cells were fused to myeloma cells (Sp2/0 cells) using a 50% PEG (polyethylene Glycol in DMEM) solution to produce hybridomas. As a control, $10 \times 10^6$ non-depleted, non-activated splenocytes were fused to Sp2/0 cells also using 50% PEG to produce hybridomas. In each fusion the hybridomas were selected for using HAT (Hypoxanthine, Aminopterin, and Thymidine) and gentamycin containing media in Methylcellulose. The total number of hybridomas produced by the fusion experiments was counted and found to be significantly higher for the CD138-depleted, in vitro activated lymphocytes than for untreated, control splenocytes (933 total colonies versus 117 total colonies, respectively). The counts were normalized to account for any differences in the starting number of cells. In addition, the percentage of Ag-specific hybridomas produced by the CD138-depleted, in vitro activated splenocytes was significantly higher than for control splenocytes (98.98% versus 26.6%). These results indicate that the use of CD138-depleted, in vitro activated splenocytes can be used in methods for producing hybridomas to increase the total number of hybridomas and the percentage of antigen-specific hybridomas.

Example 26

Figure 9:
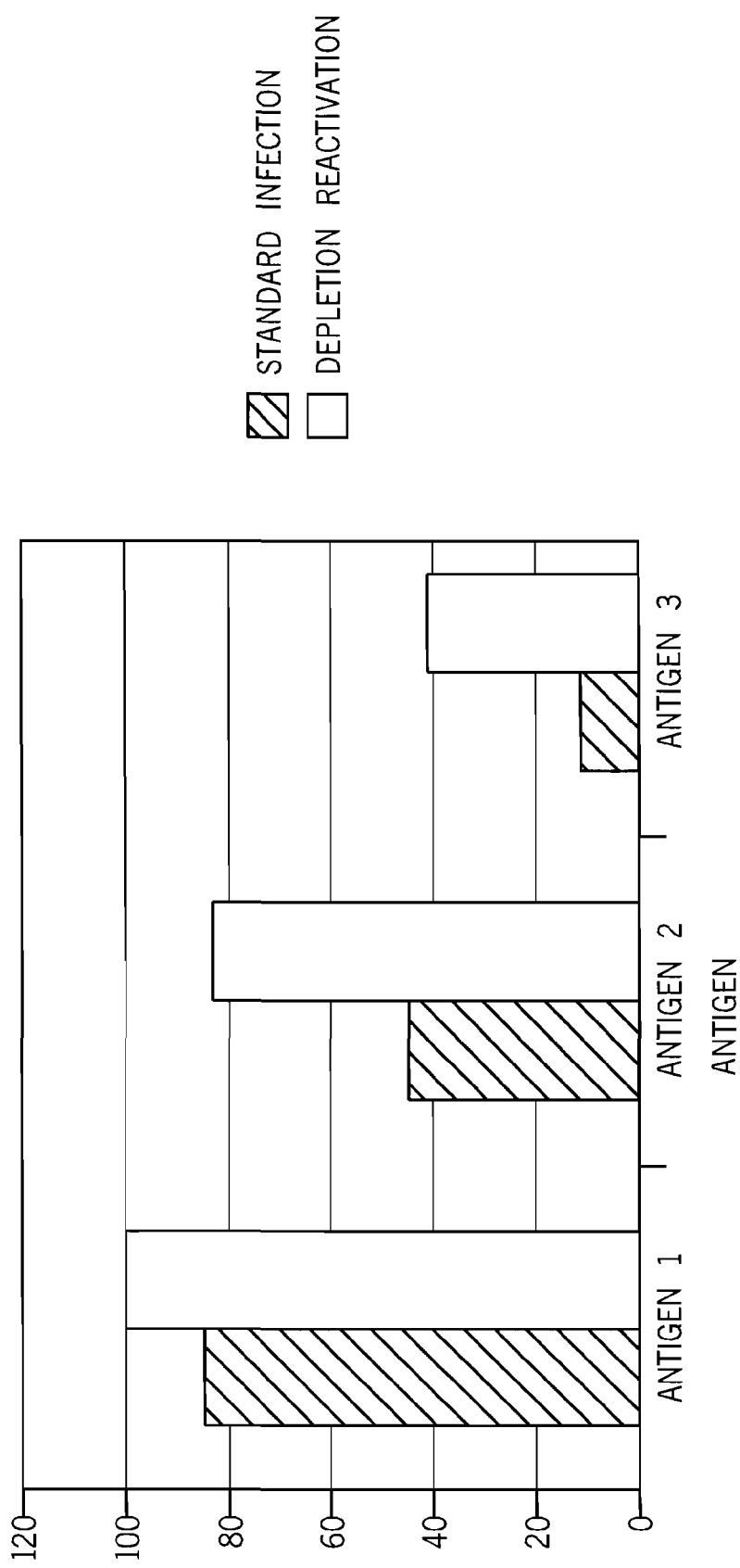
FIG. 9 demonstrates that CD138-depletion and in vitro activation of lymphocytes results in a higher frequency of ascites development upon ABL-MYC infection. Splenocytes from mice separately immunized with three unrelated antigens were CD138-depleted and in vitro activated with their respective antigen (~10 ng/ml) for three days as described in Example 23. The activated lymphocytes were then counted and infected with the ABL-MYC virus before injection into recipient mice for plasmacytomas development. As a control, an equivalent number of non-depleted, non-activated splenocytes (from mice immunized with the same antigens) were infected with ABL-MYC and injected into mice for plasmacytomas development. Plotted is the percentage of recipient mice that developed ascites from control (Standard Infection) cells and from the CD138-depleted, in vitro activated (Depletion Reactivation).
Figure 10:
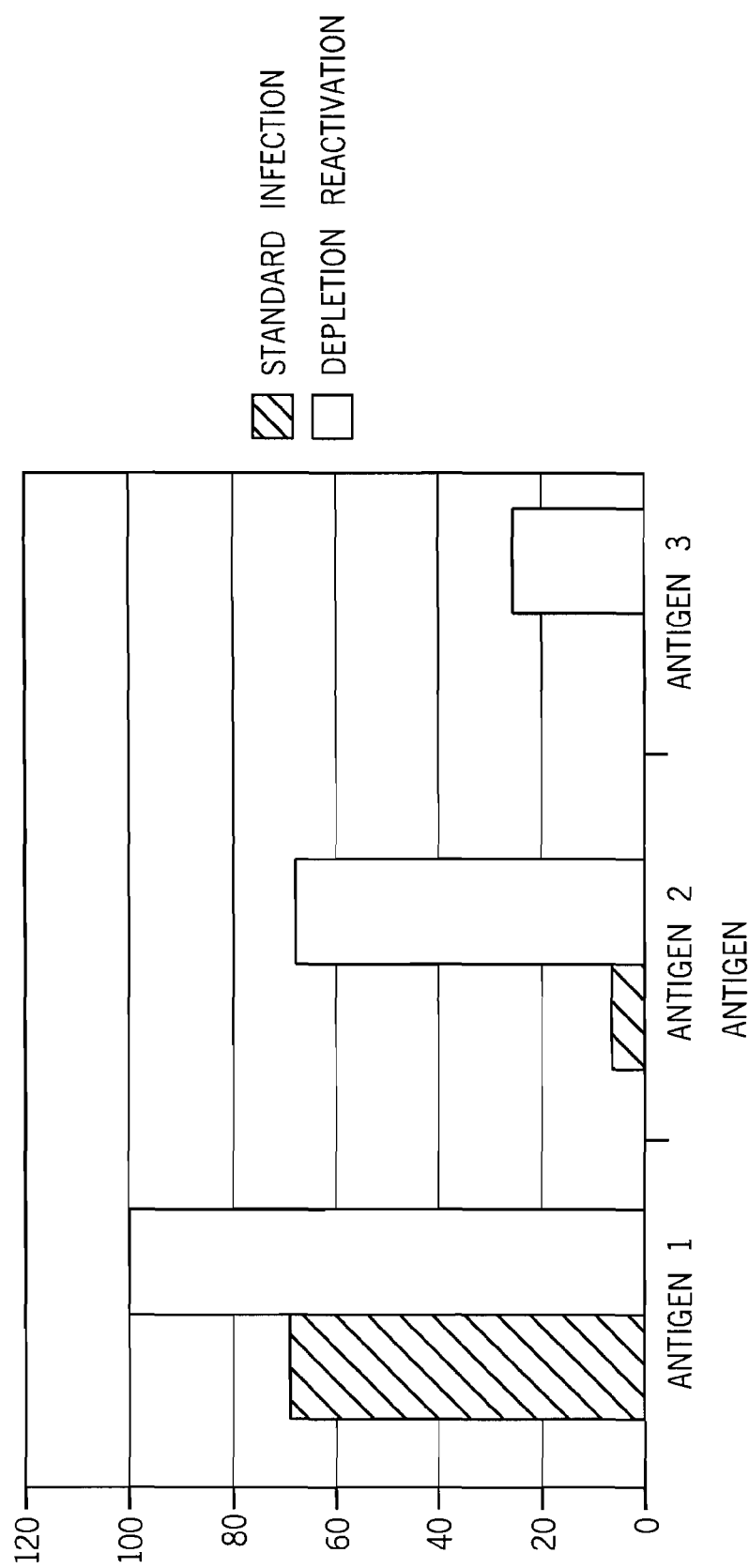
FIG. 10 demonstrates that CD138-depletion and in vitro activation of lymphocytes results in a higher frequency of antigen-specific ascites development upon ABL-MYC infection. Ascites developed as described in FIG. 9 were analyzed for antigen-specific immunoglobulin by ELISA. The figure shows the percentage of total ascites that tested positive for antigen-specific immunoglobulin.

CD138-depleted, In Vitro Activated Lymphocytes Form Antigen-Specific Plasmacytomas More Efficiently than Untreated Lymphocytes Upon Infection with ABL-MYC Splenocytes from mice separately immunized with three unrelated antigens were CD138-depleted and the depleted lymphocytes were in vitro activated with their respective antigen (~10 ng/ml) for three days as described in Example 23. The activated lymphocytes were then counted and infected with the ABL-MYC virus before injection into recipient mice for plasmacytomas development. As a control, an equivalent number of non-depleted, non-activated splenocytes (from mice immunized with the same antigens) were infected with ABL-MYC and injected into mice for plasmacytomas development. FIG. 9 shows that the CD138-depleted, in vitro activated cells were more likely to produce plasmacytoma-containing ascites than control splenocytes. For Antigen 1, 100% of the mice injected with infected cells from the depletion, activation process developed ascites as compared to 83% for the control cells. For Antigens 2 and 3, the effect of the depletion-activation process was more dramatic. CD138-depletion and in vitro activation resulted in nearly twice as many mice developing ascites for Antigen 2 compared to control cells and nearly four times as many for Antigen 3. FIG. 10 shows that the ascites develop from the depleted, activated cells were more likely to be antigen-specific than control ascites. For Antigen 1, 68% of ascites produced from control splenocytes contained Ag-specific plasmacytomas, while 100% of ascites produced from CD138-depleted, in vitro activated cells contained Ag-specific plasmacytomas. For Antigens 2 and 3, 6% and zero percent, respectively, of the ascites produced from control splenocytes contained Ag-specific plasmacytomas, while 67% and 25% of ascites, respectively, produced from CD138-depleted, in vitro activated cells contained Ag-specific plasmacytomas. These results indicate that the use of CD138-depleted, in vitro activated lymphocytes can be used in methods for producing plasmacytomas, increasing the frequency of plasmacytoma development and the frequency of antigen-specific plasmacytomas. These data also show that this novel method can lead to antibody-producing plasmacytomas where standard methods have failed.

Example 27

Demonstration of Antigen Specific Activation and Reactivation by ELISPOT

Figure 11:
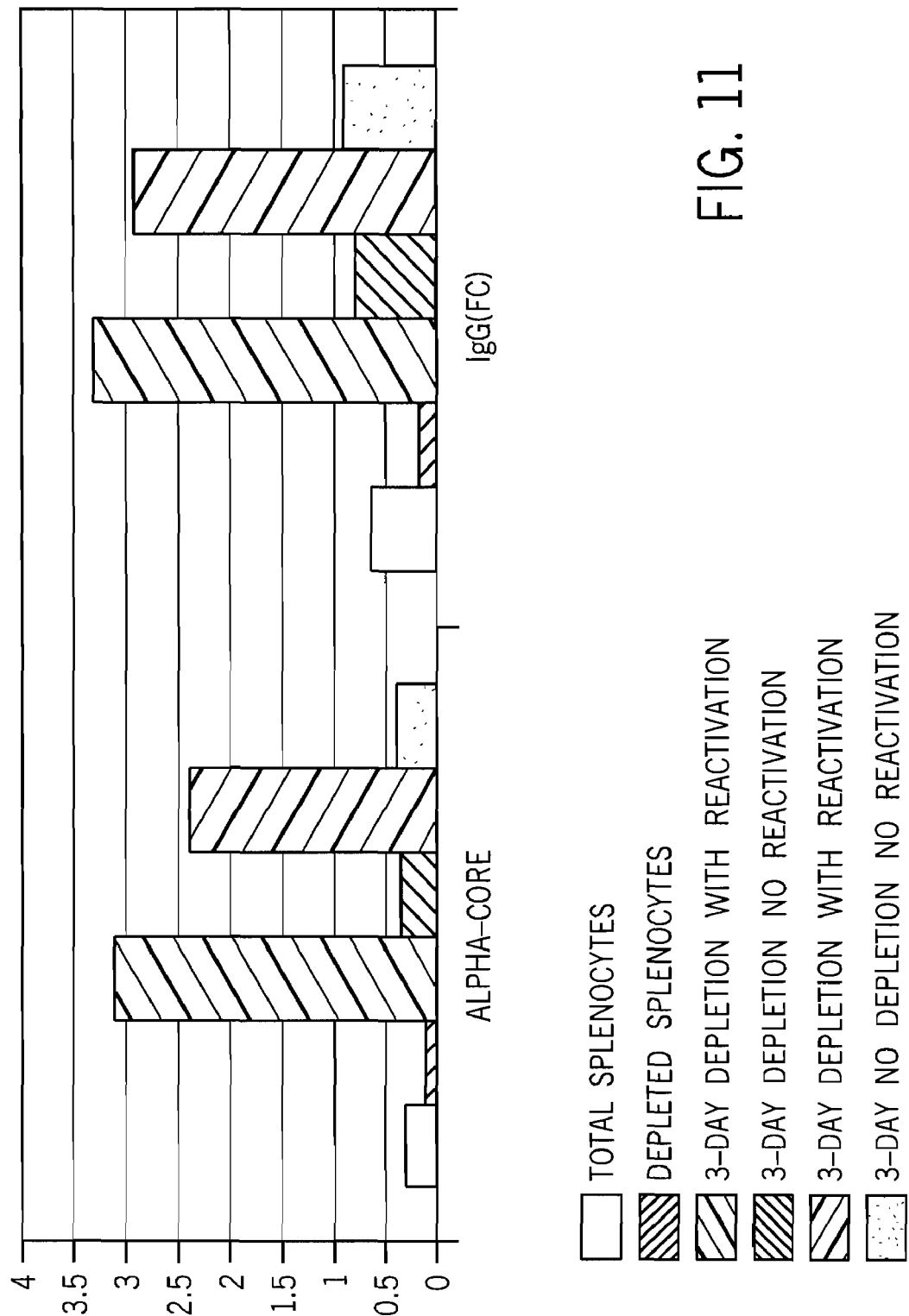
FIG. 11 demonstrates that both CD138-depletion and antigen-activation are important for obtaining activated B lymphocytes. Splenocytes isolated from mice immunized with the α-subunit of *E. coli* RNA polymerase were subjected to a 3-day antigen activation with or without prior CD138-depletion as described in FIG. 4. Cells were subjected to antigen-specific (alpha-core) and total IgG (IgG(Fc)) ELISPOT. Data is plotted as the percentage of total cells that secrete immunoglobulin. Data is shown for control, untreated splenocytes (Total Splenocytes), CD138-depleted splenocytes with no activation period (Depleted Splenocytes), CD138-depleted cells activated for 3-days in the presence (3-day Depletion with Reactivation) or absence (3-day Depletion no Reactivation), and Non-depleted cells activated for 3-days in the presence (3-day No Depletion with Reactivation) or absence (3-day No Depletion no Reactivation)

Splenocytes isolated from mice immunized with the α-subunit of *E. coli* RNA polymerase were subjected to a 3-day antigen activation with or without prior CD138-depletion. FIG. 11 depicts ELISPOT data for control, untreated splenocytes (Total Splenocytes), CD138-depleted splenocytes with no activation period (Depleted Splenocytes), CD138-depleted cells activated for 3-days in the presence (3-day Depletion with Reactivation) or absence (3-day Depletion no Reactivation), and Non-depleted cells activated for 3-days in the presence (3-day No Depletion with Reactivation) or absence (3-day No Depletion no Reactivation), The data indicate that Ag-specific, IgG secreting cells were enriched more than 10-fold in the CD138-depleted, antigen-activated population compared to non-fractionated splenocytes (total splenocytes). In addition, depletion plus activation leads to ~20% more immunoglobulin secreting cells (e.g. activated B-lymphocytes) than antigen-activation in absence of depletion.

What is claimed is:

1. A method for producing immortalized antigen-specific plasma cells, comprising:
   a) immunizing an animal and isolating splenocytes from the animal;
   b) depleting the isolated splenocytes of CD138-positive cells to obtain depleted immunized cells;
   c) contacting the depleted immunized cells with an activating agent to obtain activated, antigen-specific B-lymphocytes; and
   d) immortalizing the activated, antigen-specific B-lymphocytes, thereby producing the immortalized antigen-specific plasma cells.

2. The method of claim 1, wherein the activating agent comprises the antigen.

3. The method of claim 2, wherein the activating agent further comprises antigen-specific T-cells.

4. The method of claim 2, wherein the activating agent further comprises dendritic cells.

5. The method of claim 2, wherein the activating agent further comprises macrophages.

6. The method of claim 2, wherein the activating agent further comprises a cytokine.

7. The method of claim 6, wherein the cytokine comprises IL-4.

8. The method of claim 2, wherein the activating agent further comprises an antibody.

9. The method of claim 8, wherein the antibody is an antibody against CD40.

10. The method of claim 8, wherein the antibody is an antibody against IgM.

11. The method of claim 1, wherein the depleted immunized cells and the activating agent are contacted for at least about 2 days.

12. The method of claim 1, wherein step d) comprises transfecting the activated, antigen-specific B-lymphocytes with a viral vector that transforms the transfected cells to obtain plasmacytoma cells.

13. The method of claim 12, wherein transfecting comprises infecting the activated, antigen-specific B-lymphocytes with the viral vector and the viral vector comprises one or more oncogenes.

14. The method of claim 1, further comprising growing the immortalized antigen-specific plasma cells to obtain antibodies that specifically bind to the antigen.

15. The method of claim 12, further comprising growing the plasmacytoma cells to obtain monoclonal antibodies that specifically bind to the antigen.

16. The method of claim 1, wherein the animal is a mouse.

17. A method comprising:
   a) immunizing an animal and isolating splenocytes from the animal;
   b) depleting the isolated splenocytes of CD138-positive cells to obtain depleted immunized cells;
   c) contacting the depleted immunized cells with an activating agent to obtain activated, antigen-specific B-lymphocytes; and
   d) immortalizing the activated, antigen-specific B-lymphocytes.

18. The method of claim 17, wherein the activating agent comprises the antigen.

19. The method of claim 18, wherein the activating agent further comprises antigen-specific T-cells, dendritic cells, macrophages, or a mixture thereof.

20. The method of claim 18, wherein the activating agent further comprises a cytokine.

21. The method of claim 18, wherein the activating agent further comprises an antibody.

22. The method of claim 17, wherein step d) comprises transfecting the activated, antigen-specific B-lymphocytes with a viral vector that transforms the transfected cells.

23. The method of claim 17, wherein step d) comprises fusing the activated, antigen-specific B-lymphocytes and myeloma cells.

24. The method of claim 17, wherein the animal is a mouse.

* * * * *